(12) United States Patent
Dymock et al.

(10) Patent No.: US 9,062,074 B2
(45) Date of Patent: Jun. 23, 2015

(54) (9E)-15-(2-PYRROLIDIN-1-YL-ETHOXY)-7,12,25-TRIOXA-19,21,24-TRIAZA-TETRACYCLO[18.3.1.1(2.5).1(14,18)] HEXACOSA-1(24),2,4,9,14,16,18(26),20,22-NONAENE CITRATE SALT

(75) Inventors: Brian Dymock, Singapore (SG); Cheng H. Lee, Singapore (SG); Anthony D. William, Singapore (SG)

(73) Assignee: CTI BioPharma Corp., Seattle, WA (US)

( * ) Notice: Subject to any disclaimer, the term of this patent is extended or adjusted under 35 U.S.C. 154(b) by 701 days.

(21) Appl. No.: 13/384,139

(22) PCT Filed: Jul. 14, 2010

(86) PCT No.: PCT/SG2010/000265
§ 371 (c)(1),
(2), (4) Date: Apr. 6, 2012

(87) PCT Pub. No.: WO2011/008172
PCT Pub. Date: Jan. 20, 2011

(65) Prior Publication Data
US 2012/0196876 A1  Aug. 2, 2012

Related U.S. Application Data

(60) Provisional application No. 61/225,609, filed on Jul. 15, 2009.

(51) Int. Cl.
*C07D 498/18* (2006.01)
*A61K 31/395* (2006.01)

(52) U.S. Cl.
CPC .................................. *C07D 498/18* (2013.01)

(58) Field of Classification Search
None
See application file for complete search history.

(56) References Cited

FOREIGN PATENT DOCUMENTS

| CN | 101360751 A | 2/2009 |
|---|---|---|
| WO | WO-2004/078682 A2 | 9/2004 |
| WO | WO 2007/058627 A1 | 5/2007 |

OTHER PUBLICATIONS

William. Journal of Medicinal Chemistry, 2012, 55, 2623-40.*
Melnikov. Journal of Pharmaceutical Sciences, 2003, 92(10), 2140-43.*
"Rheumatoid Arthritis-Causes".http://www.mayoclinic.org/diseases-conditions/rheumatoid-arthritis/basics/causes/con-2001, accessed Sep. 5, 2014.*
First Office Action issued in Chinese Application No. 201080032627.5, together with the English Translation on Dec. 4, 2013.
International Search Report issued in International Application No. PCT/SG2010/000265.
Israeli Office Action in Hebrew, issued in Israeli Patent Application No. 213418, dated Sep. 29, 2014.
The Israeli agent letter reporting the Israeli Office Action in Israeli Patent Application No. 213418.
D. J. W. Grant (chapter 1) p. 1-10; and J. K. Guillory (chapter 5) p. 183-226, "Polymorphism in pharmaceutical solids" edited by H. G. Brittain, Marcel Dekker, (1999).
S. Byrn et al., "Pharmaceutical Solids: A Strategic Approach to Regulatory Considerations", Pharmaceutical Research, (1995), vol. 12, No. 7, p. 945-954.
Philip L. Gould, "Salt Selection for Basic Drugs", International Journal of Pharmaceutics, (1986), vol. 33, p. 201-217.
Abu T. M. Serajuddin, "Salt formation to improve drug solubility", Advanced Drug Delivery Reviews, vol. 59, 2007, p. 603-616.
P. Heinrich Stahl, "Preparation of water-soluble compounds through salt formation", The Practice of Medicinal Chemistry, 2nd ed. 2003, p. 601-615.

* cited by examiner

*Primary Examiner* — Noble Jarrell
(74) *Attorney, Agent, or Firm* — Novak Druce Connolly Bove + Quigg LLP

(57) ABSTRACT

The present invention relates to certain salts of a 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene (Compound I) which have been found to have improved properties. In particular the present invention relates to the citrate salt of this compound. The invention also relates to pharmaceutical compositions containing the citrate salt and methods of use of the citrate salt in the treatment of certain medical conditions.

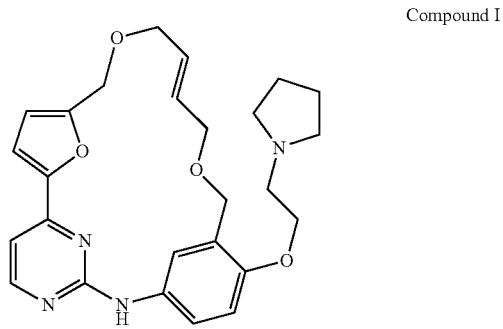

Compound I

14 Claims, 23 Drawing Sheets

(9E)-15-(2-PYRROLIDIN-1-YL-ETHOXY)-7,12,25-TRIOXA-19,21,24-TRIAZA-TETRACYCLO[18.3.1.1(2.5).1(14,18)]HEXACOSA-1(24),2,4,9,14,16,18(26),20,22-NONAENE CITRATE SALT

CROSS REFERENCE TO RELATED APPLICATIONS

This application is a National Phase filing under 35 U.S.C. §371 of International Application No. PCT/SG2010/000265, filed Jul. 14, 2010, which claims priority to U.S. Provisional Patent Application No. 61/225,609, filed Jul. 15, 2009. The entire contents of each of the above-applications are incorporated herein by reference.

FIELD

The present invention relates to the citrate salt of 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene. In addition the present invention relates to pharmaceutical compositions containing the citrate salt and methods of use of the salt in the treatment of certain medical conditions.

BACKGROUND

The compound 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene (Compound I) was first described in PCT/SG2006/000352 and shows significant promise as a pharmaceutically active agent for the treatment of a number of medical conditions. Pharmaceutical development of this compound is underway based on the activity profiles demonstrated by the compound.

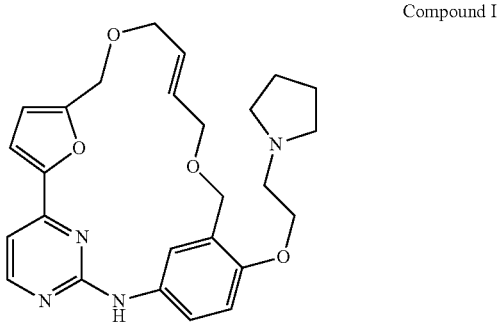 [SMILES: C1=C2COC/C=C/COCc3cc(ccc3OCCN3CCCC3)Nc3nccc(n3)C(=C1)O2]

Compound I

In the development of a drug suitable for mass production and ultimately commercial use acceptable levels of drug activity against the target of interest is only one of the important variables that must be considered. For example, in the formulation of pharmaceutical compositions it is imperative that the pharmaceutically active substance be in a form that can be reliably reproduced in a commercial manufacturing process and which is robust enough to withstand the conditions to which the pharmaceutically active substance is exposed.

From a manufacturing perspective, it is important that the commercial manufacturing process of a pharmaceutically active substance is such that the same material is produced when the same manufacturing conditions are used. In addition, it is desirable that the pharmaceutically active substance exists in a solid form where minor changes to the manufacturing conditions do not lead to major changes in the solid form of the pharmaceutically active substance produced. For example, it is important that the manufacturing process produces material having the same crystalline properties on a reliable basis, and also that the process produces material having the same level of hydration.

In addition, it is important that the pharmaceutically active substance be stable to degradation, hygroscopicity and subsequent changes to its solid form. This is important to facilitate the incorporation of the pharmaceutically active ingredient into pharmaceutical formulations. If the pharmaceutically active substance is hygroscopic ("sticky") in the sense that it absorbs water over time it is almost impossible to reliably formulate the pharmaceutically active substance into a drug as the amount of substance to be added to provide the same dosage will vary greatly depending upon the degree of hydration. Furthermore, variations in hydration or solid form ("polymorphism") can lead to changes in physico-chemical properties, such as solubility or dissolution rate, which can in turn lead to inconsistent oral absorption in a patient.

Accordingly, chemical stability, solid state stability, and "shelf life" of the pharmaceutically active agent are very important factors. In an ideal situation the pharmaceutically active agent and any compositions containing it, should be capable of being effectively stored over appreciable periods of time without exhibiting a significant change in the physico-chemical characteristics of the active component such as its activity, moisture content, solubility characteristics, solid form and the like.

In relation to 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene initial studies were carried out on the hydrochloride salt and indicated that polymorphism was prevalent, with the compound being found to adopt more than one crystalline form depending upon the manufacturing conditions. In addition it was observed that the ratio of the polymorphs varied from batch to batch even when the manufacturing conditions remained constant. These batch-to-batch inconsistencies made the hydrochloride salt less desirable from a commercial viewpoint.

Accordingly it would be desirable to develop salts of 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene which overcome or ameliorate one or more of the above identified problems.

SUMMARY

The present invention provides a citrate salt (citric acid salt) of 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene.

In some embodiments the salt is crystalline.

In some embodiments the salt is the 1:1 citrate salt. In some embodiments the citrate salt shows on X-ray diffraction a peak on the 2theta scale at 22.4°±0.5°.

In some embodiments the citrate salt also shows on X-ray diffraction peaks on the 2theta scale at 10.0°±0.5°, 15.6°±0.5° and 17.2°±0.5°.

In some embodiments the citrate salt shows on X-ray diffraction at least four peaks on the 2theta scale selected from the group consisting of 7.9°±0.5°, 10.0°±0.5°, 15.6°±0.5°, 15.9°±0.5°, 16.8°±0.5°, 17.2°±0.5°, 21.1°±0.5°, and 22.4°±0.5°.

In some embodiments the citrate salt shows on X-ray diffraction at least 6 peaks on the 2theta scale selected from the group consisting of 7.9°±0.5°, 10.0°±0.5°, 15.6°±0.5°, 15.9°±0.5°, 16.8°±0.5°, 17.2°±0.5°, 21.1°±0.5°, and 22.4°±0.5°.

In some embodiments the citrate salt shows on X-ray diffraction peaks on the 2theta scale at 7.9°±0.5°, 10.0°±0.5°, 15.6°±0.5°, 15.9°±0.5°, 16.8°±0.5°, 17.2°±0.5°, 21.1°±0.5°, and 22.4°±0.5°.

In some embodiments the citrate salt also shows on X-ray diffraction peaks on the 2theta scale at 11.1°±0.5°, 18.1°±0.5°, 21.8°±0.5°, 23.2°±0.5°, and 27.6°±0.5°.

In some embodiments the citrate salt also shows on X-ray diffraction peaks on the 2theta scale at 7.0°±0.5°, 14.0°±0.5°, 19.0°±0.5°, 19.8°±0.5°, 23.6°±0.5°, 24.3°±0.5°, 25.2°±0.5°, 25.7°±0.5°, 26.1°±0.5°, 26.5°±0.5°, and 32.1°±0.5°.

The present invention also provides a pharmaceutical composition comprising a salt as described above.

In another embodiment the present invention provides a method of treating or preventing a proliferative disorder comprising administration of a therapeutically effective amount of a salt of the invention to a patient in need thereof. In some embodiments the proliferative disorder is cancer.

In another embodiment the present invention provides the use of a salt of the invention in the treatment of a proliferative disorder. In some embodiments the proliferative disorder is cancer.

In another embodiment the present invention provides the use of a salt of the invention in the manufacture of a medicament for the treatment of a proliferative disorder. In some embodiments the proliferative disorder is cancer.

DETAILED DESCRIPTION

As stated above it has now been found that certain salts of 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene exist as single robust polymorphs. In particular the present applicants have found that the citrate salt (citric acid salt) of this compound exists as a single polymorph.

Whilst it is considered that the structure of citric acid would be clear to a skilled addressee in the art in order to avoid any uncertainty the structure is shown below.

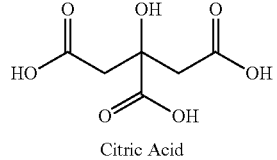

Citric Acid

Comparative, studies described herein for hydrochloride and citrate salts were carried out on the batches described in Table 1.

TABLE 1

List of hydrochloride and citrate salt batches used for comparative studies

| Batch Number | Salt | Crystallisation Solvent | Solid Form Comment |
|---|---|---|---|
| 1 | HCl | THF | Crystalline |
| 2 | HCl | MeCN | Crystalline most signals different from Batch 1 |
| 3 | HCl | Acetone | Crystalline most signals different from Batches 1 and 2 |
| 4 | Citrate | THF | Crystalline Form 1 |
| 5 | Citrate | MeCN | Crystalline Form 1 |
| 6 | Citrate | Acetone | Crystalline Form 1 |
| 7 | Citrate | Acetone | Crystalline Form 1 |
| 8 | Citrate | Acetone | Crystalline Form 1 |

Initial studies into compound 1 involved the hydrochloride salt. It was found as summarized below, that the initially prepared hydrochloride salt produces an inconsistent solid form with significant variability in the X-ray powder diffraction (XRPD) data.

Figure 1:
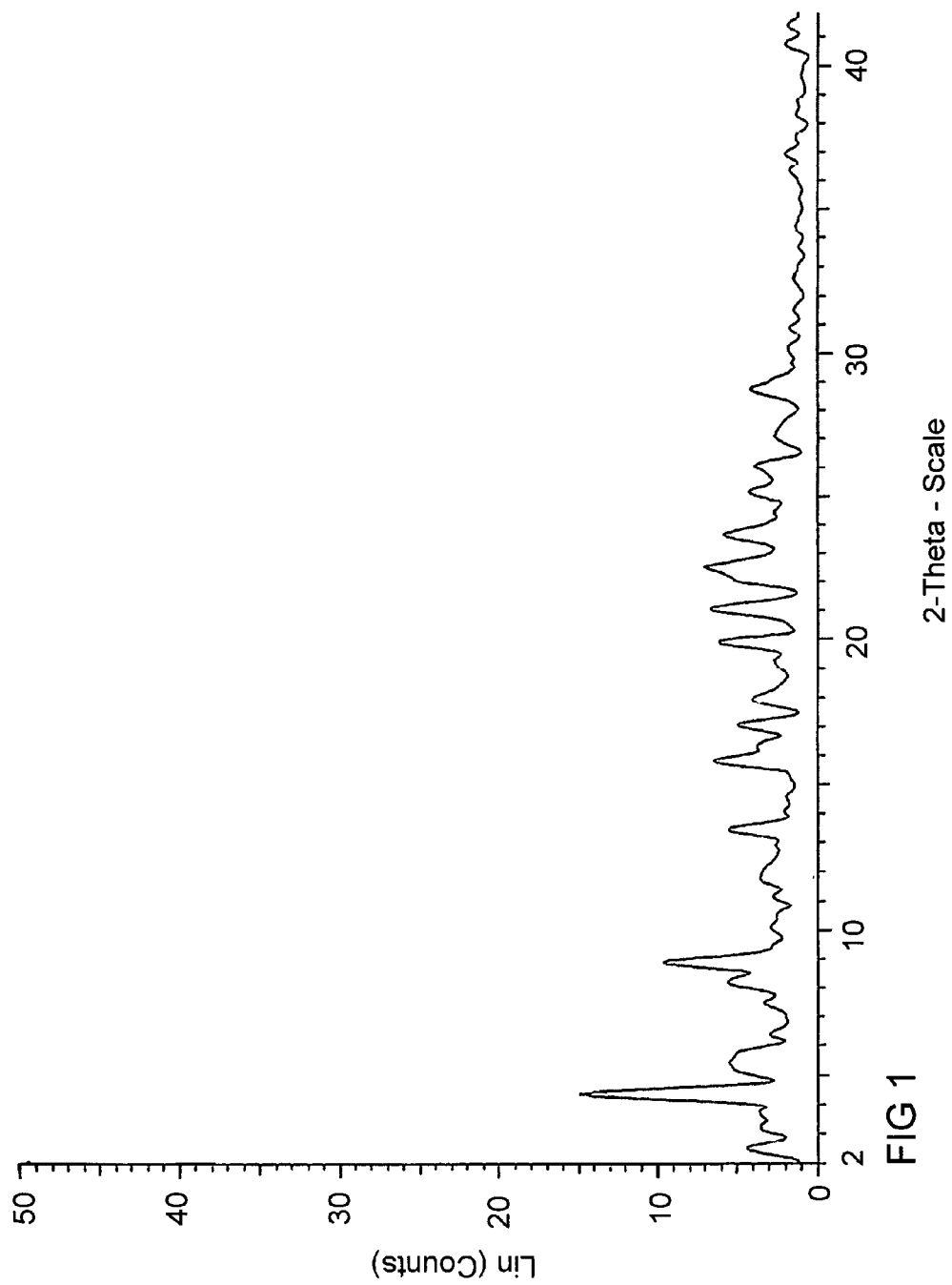
FIG. 1 shows high resolution X-ray Powder Diffraction (XRPD) diffractograms for Batch 1, HCl salt prepared in THF.
Figure 2:
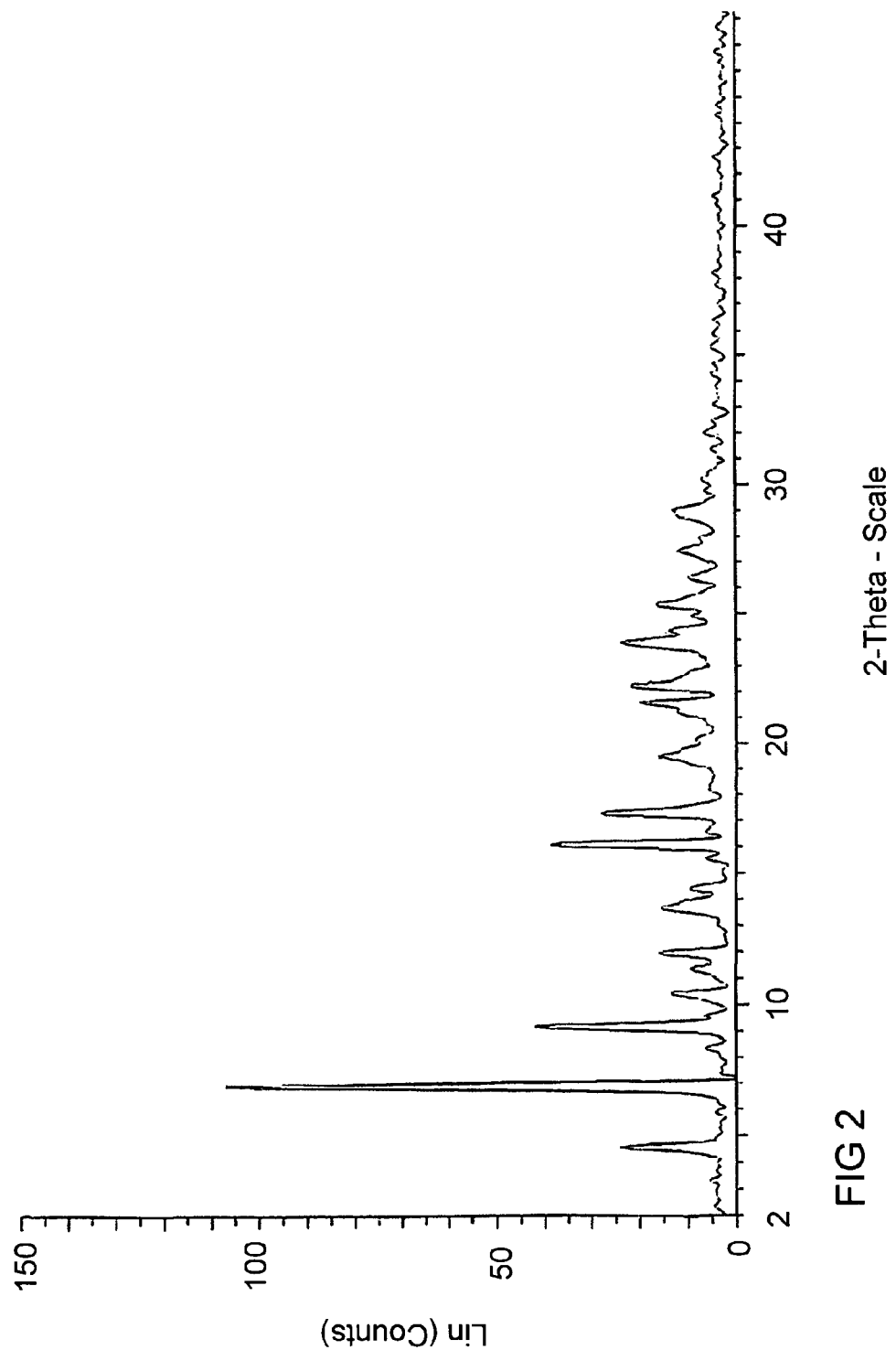
FIG. 2 shows high resolution X-ray Powder Diffraction (XRPD) diffractograms for Batch 2, HCl salt prepared in MeCN.
Figure 3:
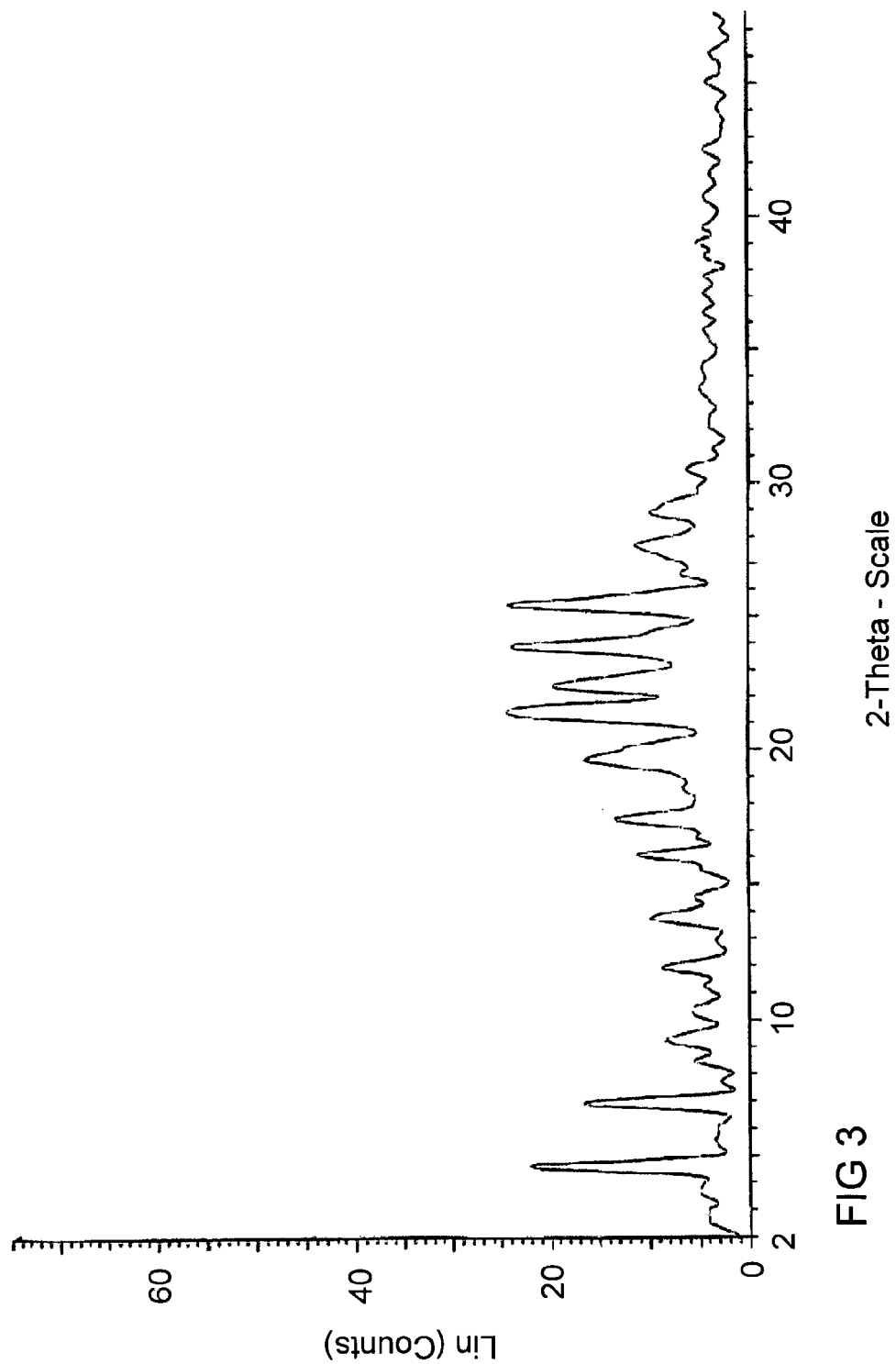
FIG. 3 shows high resolution X-ray Powder Diffraction (XRPD) diffractograms for Batch 3, HCl salt prepared in Acetone.
Figure 4:
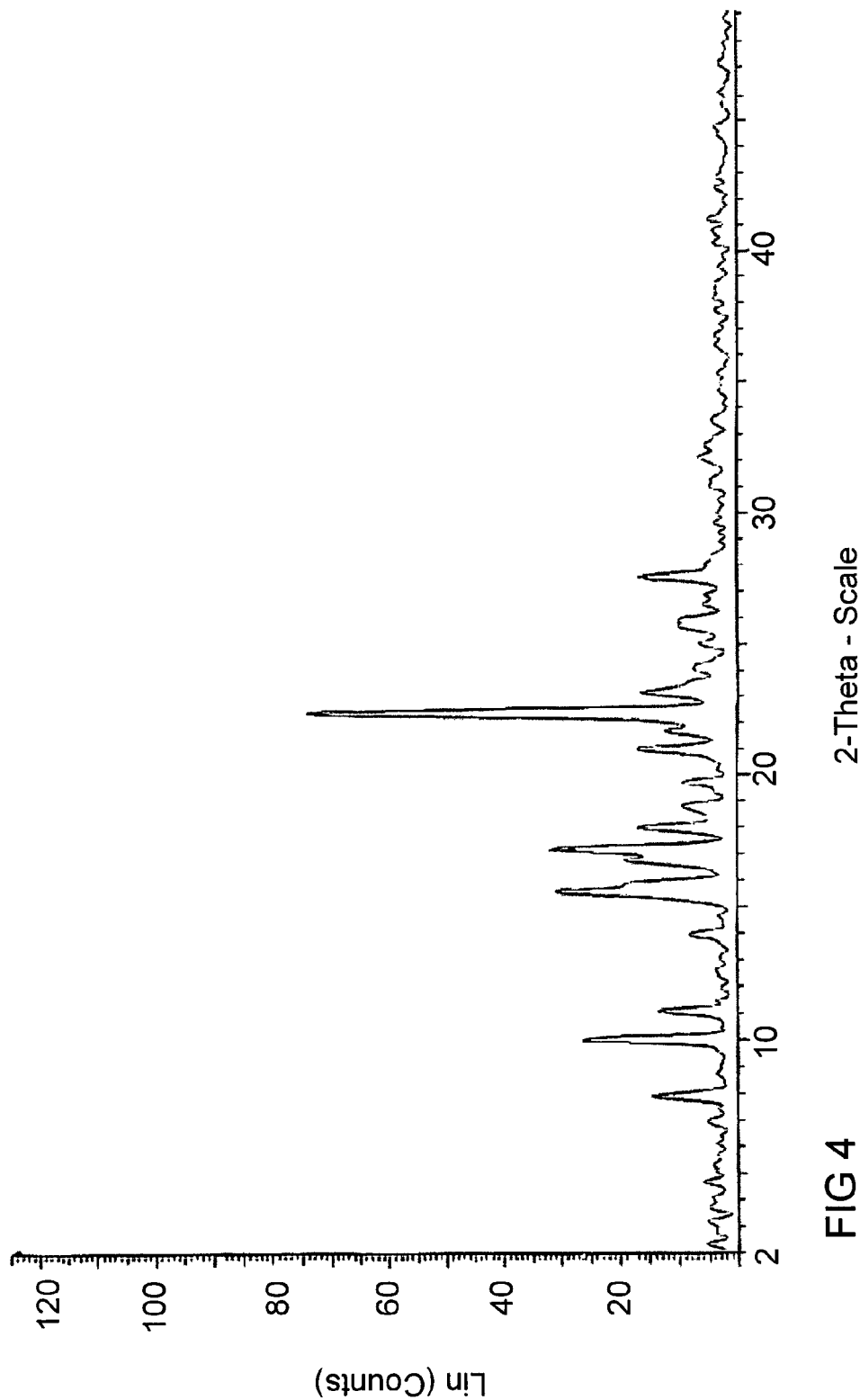
FIG. 4 shows high resolution X-ray Powder Diffraction (XRPD) diffractograms for Batch 4, Citrate salt prepared in THF.
Figure 5:
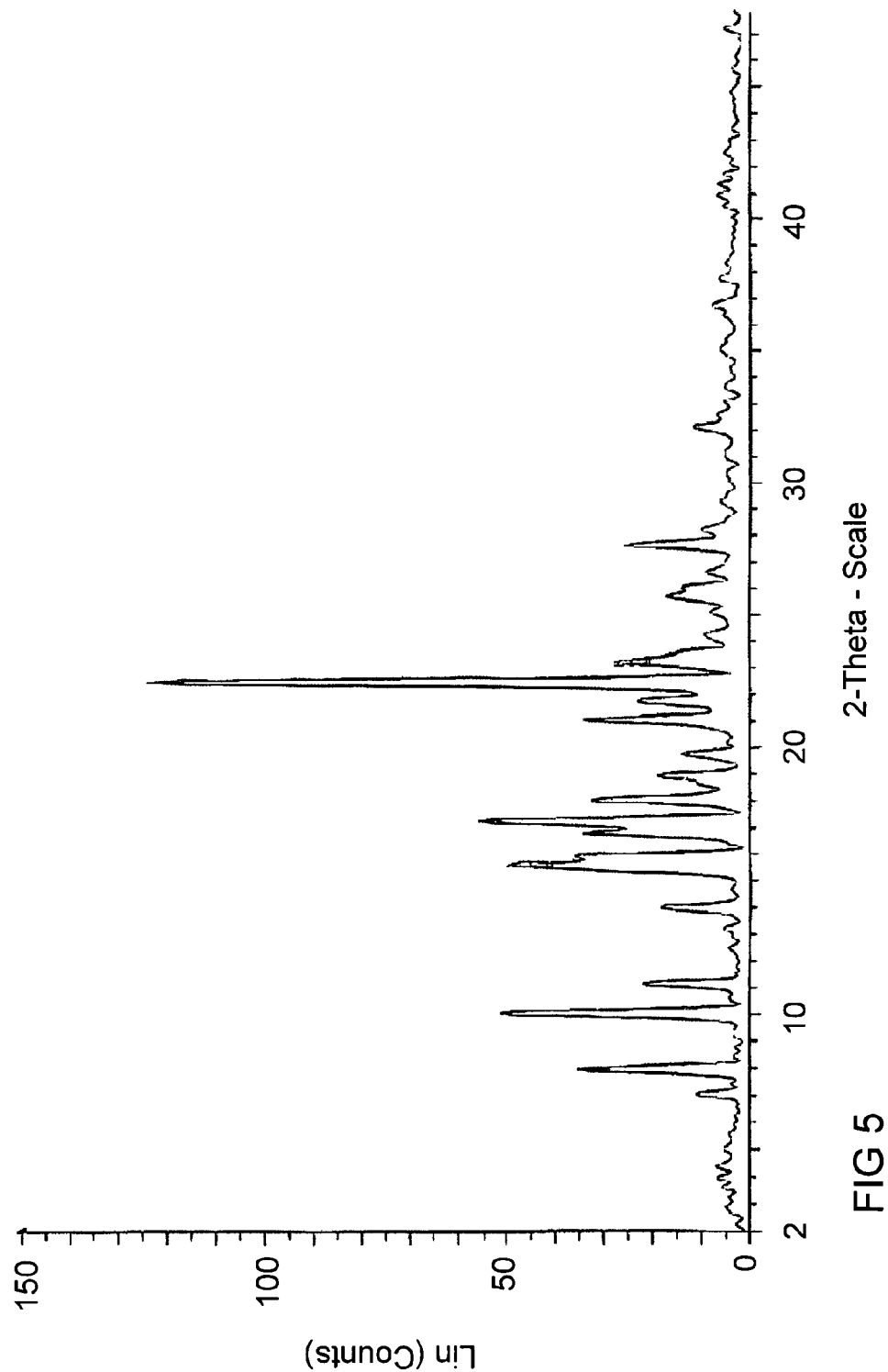
FIG. 5 shows high resolution X-ray Powder Diffraction (XRPD) diffractograms for Batch 5, Citrate salt prepared in MeCN.
Figure 6:
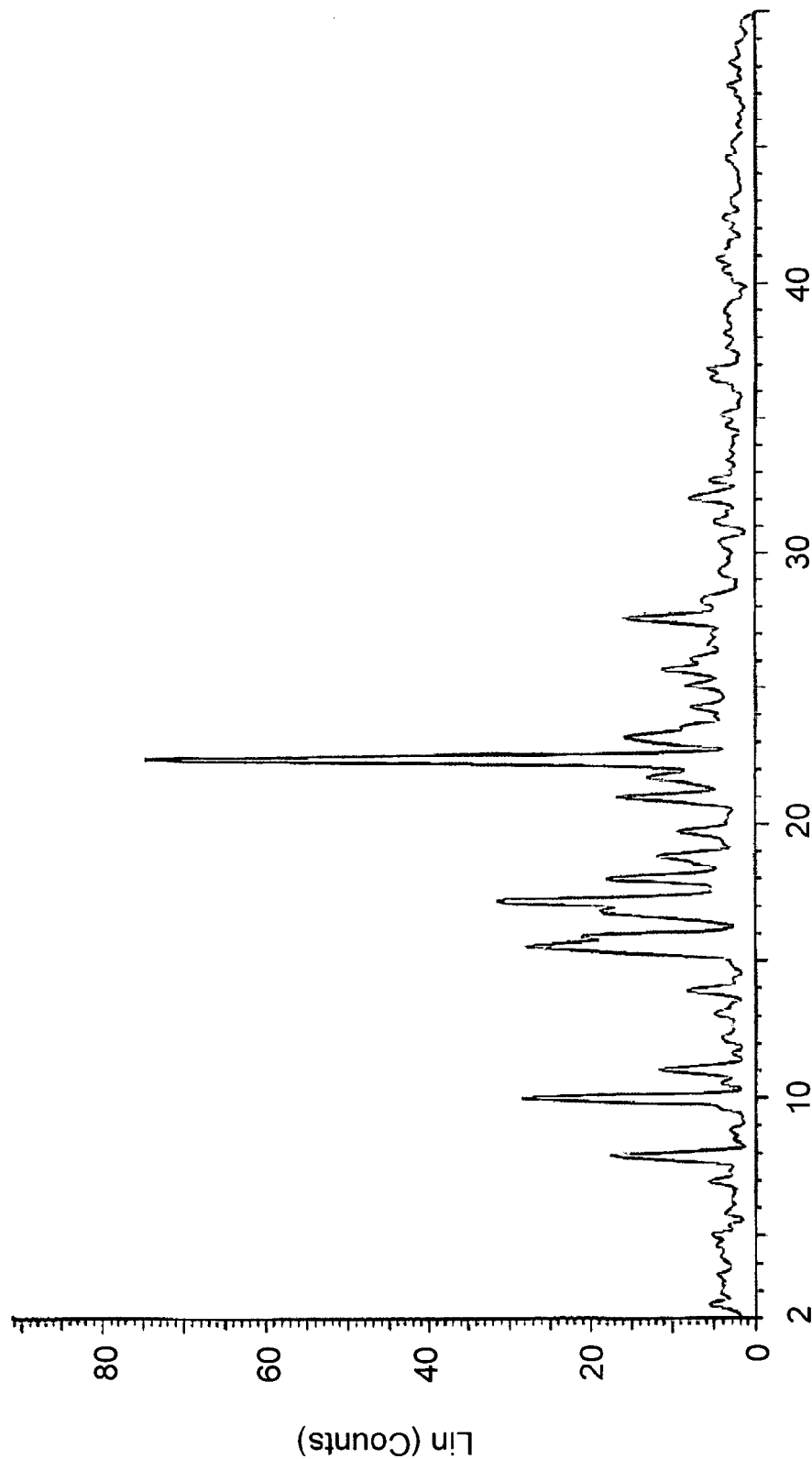
FIG. 6 shows high resolution X-ray Powder Diffraction (XRPD) diffractograms for Batch 6, Citrate salt prepared in Acetone.
Figure 7:
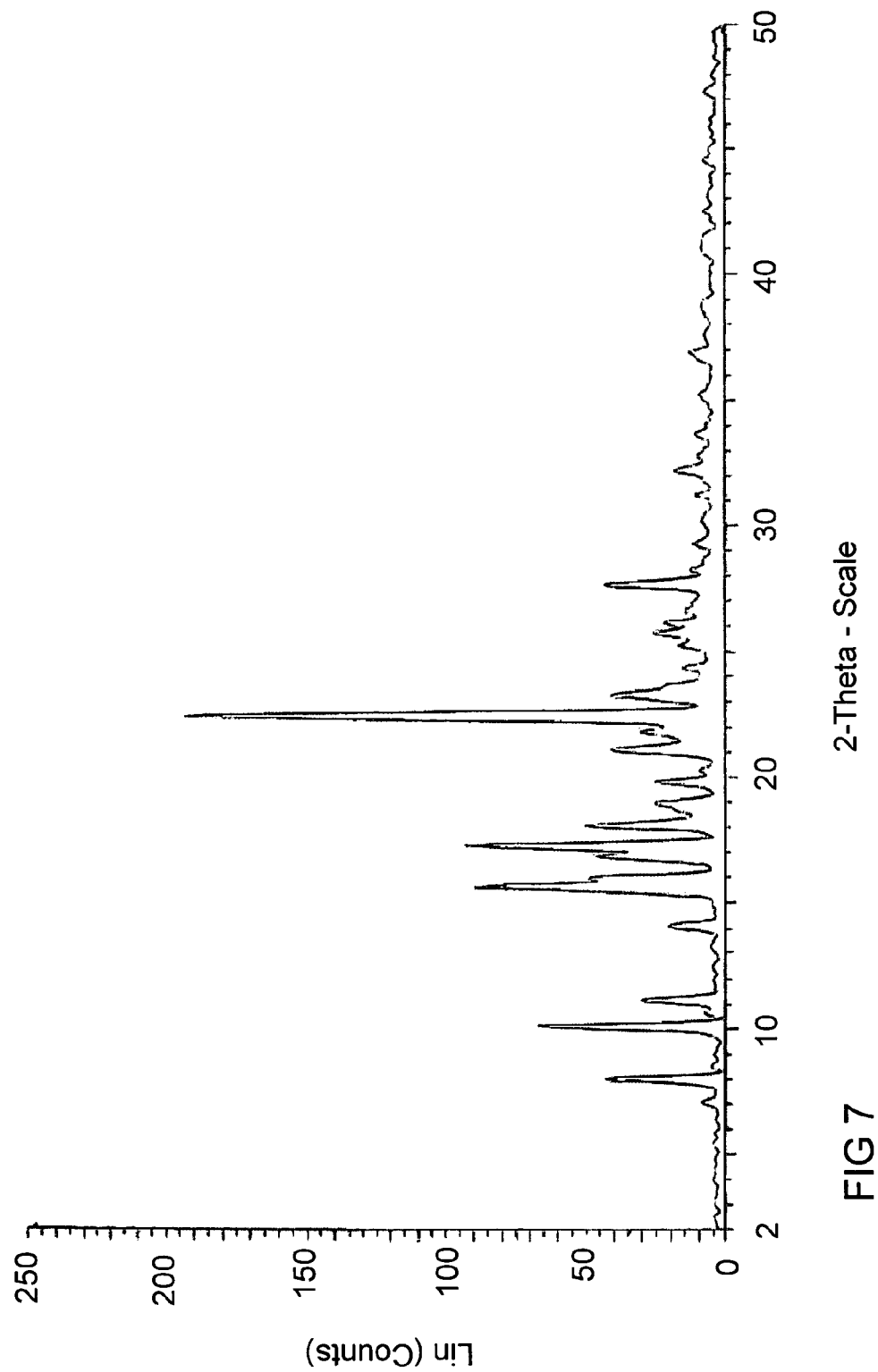
FIG. 7 shows high resolution X-ray Powder Diffraction (XRPD) diffractograms for Batch 7, Citrate salt prepared in Acetone (20 g scale).
Figure 8:
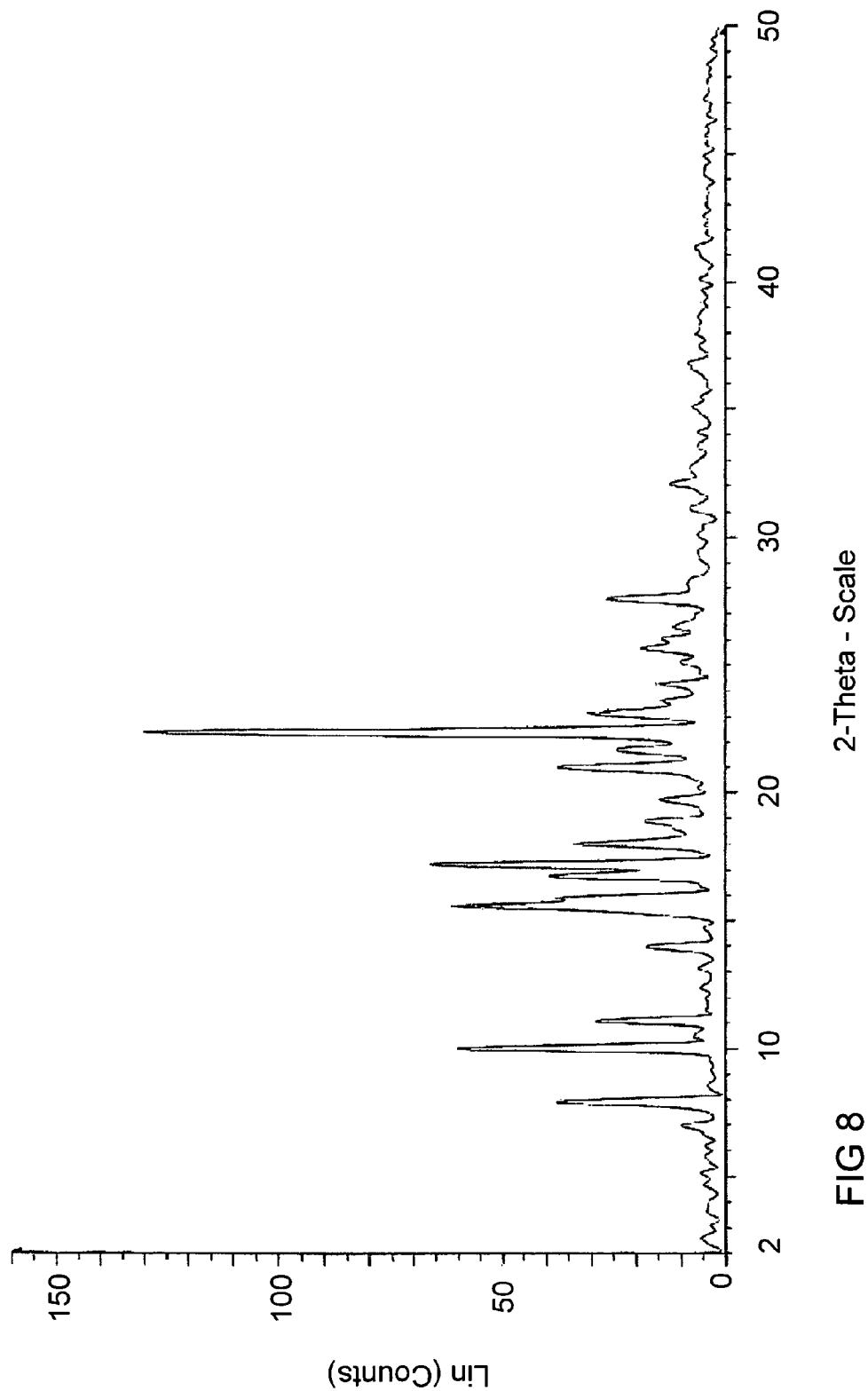
FIG. 8 shows high resolution X-ray Powder Diffraction (XRPD) diffractograms for Batch 8, Citrate salt prepared in Acetone (20 g scale.

Compound 1 as the hydrochloride salt was prepared in 3 different solvents giving Batch 1 (prepared in THF), Batch 2 (prepared in acetonitrile) and Batch 3 (prepared in acetone) as crystalline materials. FIGS. 1, 2 and 3 show significant variability in the XRPD diffractograms between these batches indicating that there is general inconsistency in the crystalline structure of these HCl salts even when prepared under similar conditions in different solvents.

As a result of the unacceptable variability observed with the hydrochloride salt as discussed above an alternative robust, solid form was required. Further discovery endeavours identified the citrate salt as being one such robust solid form.

Five batches of 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene citrate were characterised. The results of the analysis are shown in the following Examples.

X-ray Powder Diffraction (XRPD) was used to characterize the citrate salts of compound 1. A list of significant X-ray diffraction peaks for the citrate salts of the invention, collected under high resolution conditions, is included in Table 2.

TABLE 2

List of significant X-ray diffraction peaks for the citrate salt

| Position of Peak (2-theta°, ±0.5°) | Relative intensity |
| --- | --- |
| 7.0 | weak |
| 7.9 | strong |
| 10.0 | strong |
| 11.1 | medium |
| 14.0 | medium |
| 15.6 | strong |
| 15.9 | strong |
| 16.8 | strong |
| 17.2 | strong |
| 18.1 | strong |
| 19.0 | medium |
| 19.8 | medium |
| 21.1 | strong |
| 21.8 | medium |
| 22.4 | strong |
| 23.2 | medium |
| 23.6 | medium |
| 24.3 | medium |
| 25.2 | weak |
| 25.7 | medium |
| 26.1 | medium |
| 26.5 | weak |
| 27.6 | strong |
| 32.1 | weak |

As can be seen the citrate salt may be characterised as showing on X-ray diffraction a peak on the 2theta scale at $22.4°\pm0.5°$.

The citrate salt may also be characterised as showing on X-ray diffraction peaks on the 2theta scale at $10.0°\pm0.5°$, $15.6°\pm0.5°$ and $17.2°\pm0.5°$.

In some embodiments the citrate salt may be further characterised as showing on X-ray diffraction at least four peaks on the 2theta scale selected from the group consisting of $7.9°\pm0.5°$, $10.0°\pm0.5°$, $15.6°\pm0.5°$, $15.9°\pm0.5°$, $16.8°\pm0.5°$, $17.2°\pm0.5°$, $21.1°\pm0.5°$, and $22.4°\pm0.5°$.

In some embodiments the citrate salt may be further characterised as showing on X-ray diffraction at least 6 peaks on the 2theta scale selected from the group consisting of $7.9°\pm0.5°$, $10.0°\pm0.5°$, $15.6°\pm0.5°$, $15.9°\pm0.5°$, $16.8°\pm0.5°$, $17.2°\pm0.5°$, $21.1°\pm0.5°$, and $22.4°\pm0.5°$.

In some embodiments the citrate salt may be further characterised as showing X-ray diffraction peaks on the 2theta scale at $7.9°\pm0.5°$, $10.0°\pm0.5°$, $15.6°\pm0.5°$, $15.9°\pm0.5°$, $16.8°\pm0.5°$, $17.2°\pm0.5°$, $21.1°\pm0.5°$, and $22.4°\pm0.5°$.

In some embodiments the citrate salt also shows on X-ray diffraction peaks on the 2theta scale at $11.1°\pm0.5°$, $18.1°\pm0.5°$, $21.8°\pm0.5°$, $23.2°\pm0.5°$, and $27.6°\pm0.5°$.

In some embodiments the citrate salt may be further characterised as showing X-ray diffraction peaks on the 2theta scale at $7.9°\pm0.5°$, $10.0°\pm0.5°$, $11.1°\pm0.5°$, $15.6°\pm0.5°$, $15.9°\pm0.5°$, $16.8°\pm0.5°$, $17.2°\pm0.5°$, $18.1°\pm0.5°$, $21.8°\pm0.5°$, $21.1°\pm0.5°$, $22.4°\pm0.5°$, $23.2°\pm0.5°$, and $27.6°\pm0.5°$.

Whilst the peaks discussed above are the characteristic peaks, the citrate salt may also show on X-ray diffraction peaks on the 2theta scale at $7.0°\pm0.5°$, $14.0°\pm0.5°$, $19.0°\pm0.5°$, $19.8°\pm0.5°$, $23.6°\pm0.5°$, $24.3°\pm0.5°$, $25.2°\pm0.5°$, $25.7°\pm0.5°$, $26.1°\pm0.5°$, $26.5°\pm0.5°$, and $32.1°\pm0.5°$.

As will be appreciated by the skilled worker in the field, the relative intensities of the diffractions can vary depending on a number of factors such as the method of the sample preparation and the type of the instrument used. In addition in certain instances some of the peaks referred to above may not be detectable.

The salts of the present invention may be produced by reaction of the free base of compound 1 with citric acid in an appropriate solvent and recovering from the reaction mixture the resultant salt after crystallisation, precipitation or evaporation.

The reaction to form the salt may be carried out in any non-interfering solvent, or mixture of solvents, in which the free base has appropriate solubility. Examples of suitable solvents of this type include acetonitrile, tetrahydrofuran and acetone. The process typically involves dissolution of the free base in an appropriate solvent at elevated temperature such as greater than 20° C. In some embodiments, e.g. acetone, the free base is dissolved in the solvent at a temperature of about 56° C. In some embodiments, e.g. acetonitrile, the free base is dissolved in the solvent at a temperature of about 82° C.

Once the free base has been dissolved in the appropriate solvent the process then involves the addition of a suitable amount of the acid. The acid is usually added as a solution in an appropriate solvent, usually the same solvent used to dissolve the free base. The amount of acid may vary although typically the amount of acid used is a stoichiometric equivalent or a slight stoichiometric excess. Following addition of the acid the process then typically involves stirring of the reaction mixture at the addition temperature for a period of 1 hour, followed by cooling of the reaction mixture to a temperature below the reaction temperature to facilitate crystallization. Once the desired level of crystal formation has occurred the crystals may be isolated by filtration and dried using normal means in the art.

Another embodiment of the present invention provides the use of the salts of the invention in the treatment of proliferative disorders. The formulations and methodology for the use of compounds of this type and the disorders that may be treated thereby are as disclosed in PCT/SG2006/000352.

The present invention will now be described with reference to the following non-limiting examples. Hydrochloride salts were prepared as discussed above for comparative examples and analysed in an analogous manner.

Example 1

Formation of the HCl Salt (Batch 1) in THF as Solvent

The free base of Compound 1 (0.200 g, 0.432 mmoles, 1 eq) was added to 15 mL of THF. The solution was heated to reflux until complete dissolution was observed and maintained for 1 h. 1N HCl (0.518 mL, 0.518 mmoles, 1.2 eq) was then added slowly at reflux conditions. The mixture was refluxed for a further 15 min then cooled. Crystallization was observed on gradual cooling. The crystals were stirred at r.t for 12 h and filtered under vacuum. The product was dried under vacuum to afford 165 mg.

Example 2

Formation of the HCl Salt (Batch 2) in $CH_3CN$ as Solvent

The free base of compound 1 (0.300 g, 0.648 mmoles, 1 eq) was added to 70 mL of $CH_3CN$. The solution was heated to reflux until complete dissolution was observed and maintained for 1 h. 1N HCl (0.778 mL, 0.778 mmoles, 1.2 eq) was then added slowly at reflux conditions. The mixture was refluxed for a further 15 min then cooled. Crystallization was observed on gradual cooling. The crystals were stirred at r.t for 12 h and filtered under vacuum. The product was dried under vacuum to afford 190 mg.

Example 3

Formation of the HCl Salt (Batch 3) in Acetone as Solvent

The free base of compound 1 (0.200 g, 0.432 mmoles, 1 eq) was added to 50 mL of acetone. The solution was heated to reflux until complete dissolution was observed and maintained for 1 h. 1N HCl (0.518 mL, 0.518 mmoles, 1.2 eq) was then added slowly at reflux conditions. The mixture was refluxed for a further 15 min then cooled. Crystallization was observed on gradual cooling. The crystals were stirred at r.t for 12 h and filtered under vacuum. The product was dried under vacuum to afford 180 mg.

Example 4

Formation of the Citrate Salt (Batch 4) in THF as Solvent

The free base of compound 1 (0.300 g, 0.648 mmoles, 1 eq) was added to 12 mL of THF. The solution was heated to reflux until complete dissolution was observed and maintained for 1 h. A solution of citric acid (0.149 g, 0.778 mmoles, 1.2 eq) dissolved in 12 mL THF was then added slowly at reflux conditions. The mixture was refluxed for a further 15 min then cooled. Crystallization was observed on gradual cooling. The crystals were stirred at room temperature for 12 h and filtered under vacuum. The product was dried under vacuum to afford 250 mg.

Example 5

Formation of the Citrate Salt (Batch 5) in $CH_3CN$ as Solvent

The free base of compound 1 (0.200 g, 0.432 mmoles, 1 eq) was added to 45 mL of $CH_3CN$. The solution was heated to reflux until complete dissolution was observed and maintained for 1 h. A solution of citric acid (0.099 g, 0.518 mmoles, 1.2 eq) dissolved in 12 mL $CH_3CN$ was then added slowly at reflux conditions. The mixture was refluxed for a further 15 min then cooled. Crystallization was observed on gradual cooling. The crystals were stirred at r.t for 12 h and filtered under vacuum. The product was dried under vacuum to afford 220 mg.

Example 6

Formation of the Citrate Salt (Batch 6) in Acetone as Solvent

The free base of compound 1 (0.200 g, 0.432 mmoles, 1. eq) was added to 50 mL of acetone. The solution was heated to reflux until complete dissolution was observed and maintained for 1 h. A solution of citric acid (0.099 g, 0.518 mmoles, 1.2 eq) dissolved in 20 mL acetone was then added slowly at reflux conditions. The mixture was refluxed for a further 15 min then cooled. Crystallization was observed on gradual cooling. The crystals were stirred at r.t for 12 h and filtered under vacuum. The product was dried under vacuum to afford 198 mg.

Example 7

X-Ray Powder Diffraction Studies

Condition 1a (High Resolution)

X-Ray Powder Diffraction (XRPD) patterns were collected on a αSIEMENS D5000 diffractometer using Cu K radiation (1.54 A), 40 kV, 30 continuous scan mode with step size of 0.03° and step time-0.5 s, was θ-θmA. A range of θ employed with a sample-detector distance which gives an effective 22°-50°. The sample analysis time (would be exposed to the X-ray beam) was 13 minutes and 33 seconds. The software used for data collection was DIFFRACplus-D5000 #1 and the data were analysed and presented using Diffrac Plus-D5000 #1.

Samples run under ambient conditions were prepared as flat plate specimens using powder as prepared without grinding. Approximately 100-200 mg of the sample was lightly pressed on a glass slide to obtain a flat surface.

Condition 1b (High Resolution)

X-Ray Powder Diffraction (XRPD) patterns were collected on a Bruker AXS C2 GADDS diffractometer using Cu K☐ radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2. Samples run under ambient conditions were prepared as flat plate specimens using powder as prepared without grinding. Approximately 1-2 mg of the sample was lightly pressed on a glass slide to obtain a flat surface.

Condition 2 (Low Resolution)

Figure 9:
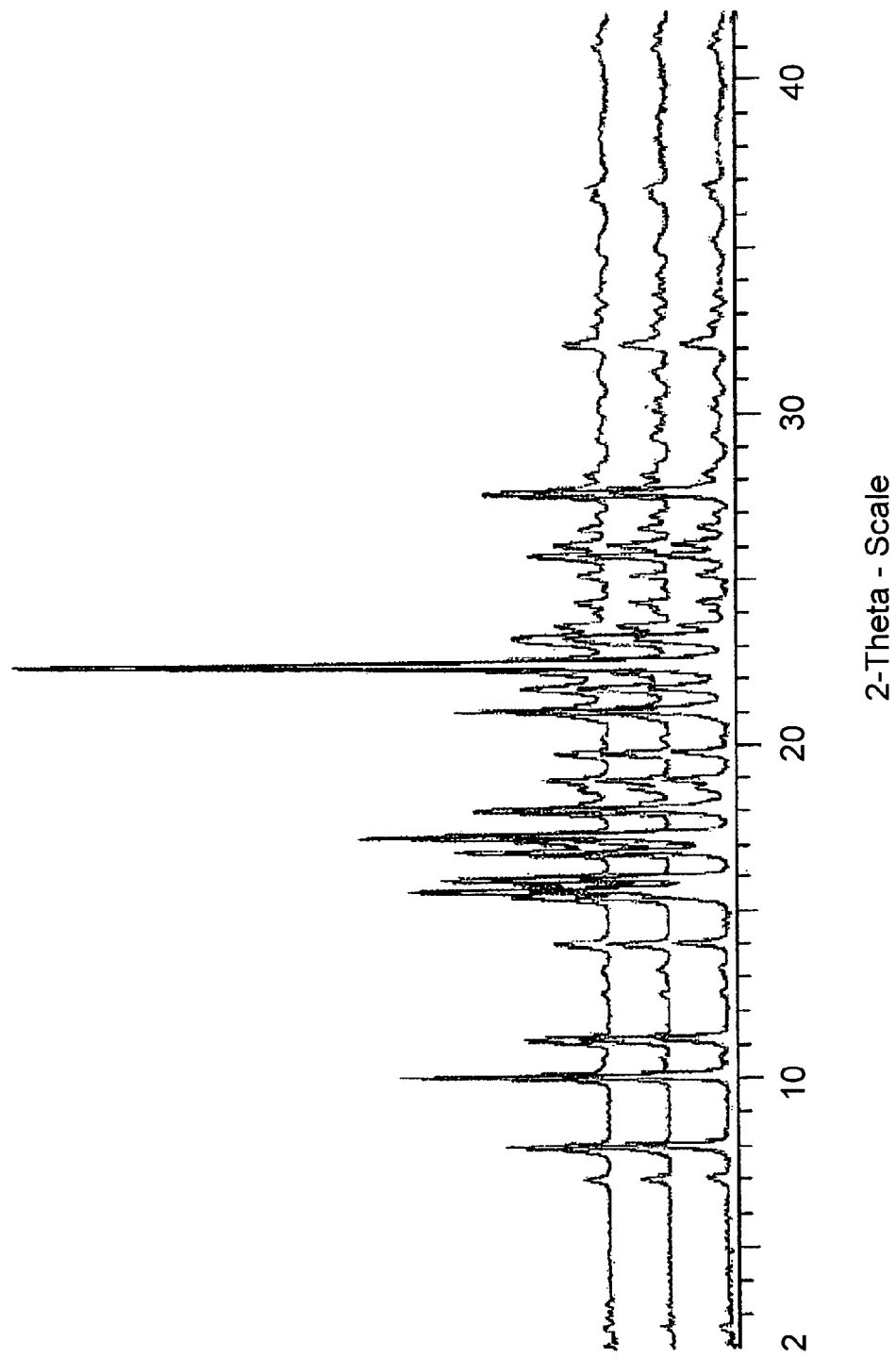
FIG. 9 shows high resolution X-ray Powder Diffraction (XRPD) diffractograms for Batches 4-6.

X-Ray Powder Diffraction patterns were also collected on a Bruker D8 diffractometer using Cu K☐ radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v 11.0.0.2 or v 13.0.0.2. Samples were run under ambient conditions as flat plate specimens using powder as received. Approximately 15 mg of the sample was gently packed into a cavity cut into polished, zerobackground (510) silicon wafer. The sample was rotated in its own plane during analysis. The details of the data collection are:

Angular range: 2 to 42 °2θ
Step size: 0.05 °2θ
Collection time: 0.5 s.step$^{-1}$ High resolution XRPD traces (Condition 1a) were obtained for each of the samples, and the results shown in FIGS. 4-8 show that the five samples of citrate salt are all of the same crystalline phase. Data for Batches 4-6 were also collected under Condition 1b and FIG. 9 shows an overlay indicating the patterns are very similar which shows they are all of the same crystalline phase.

Figure 10:
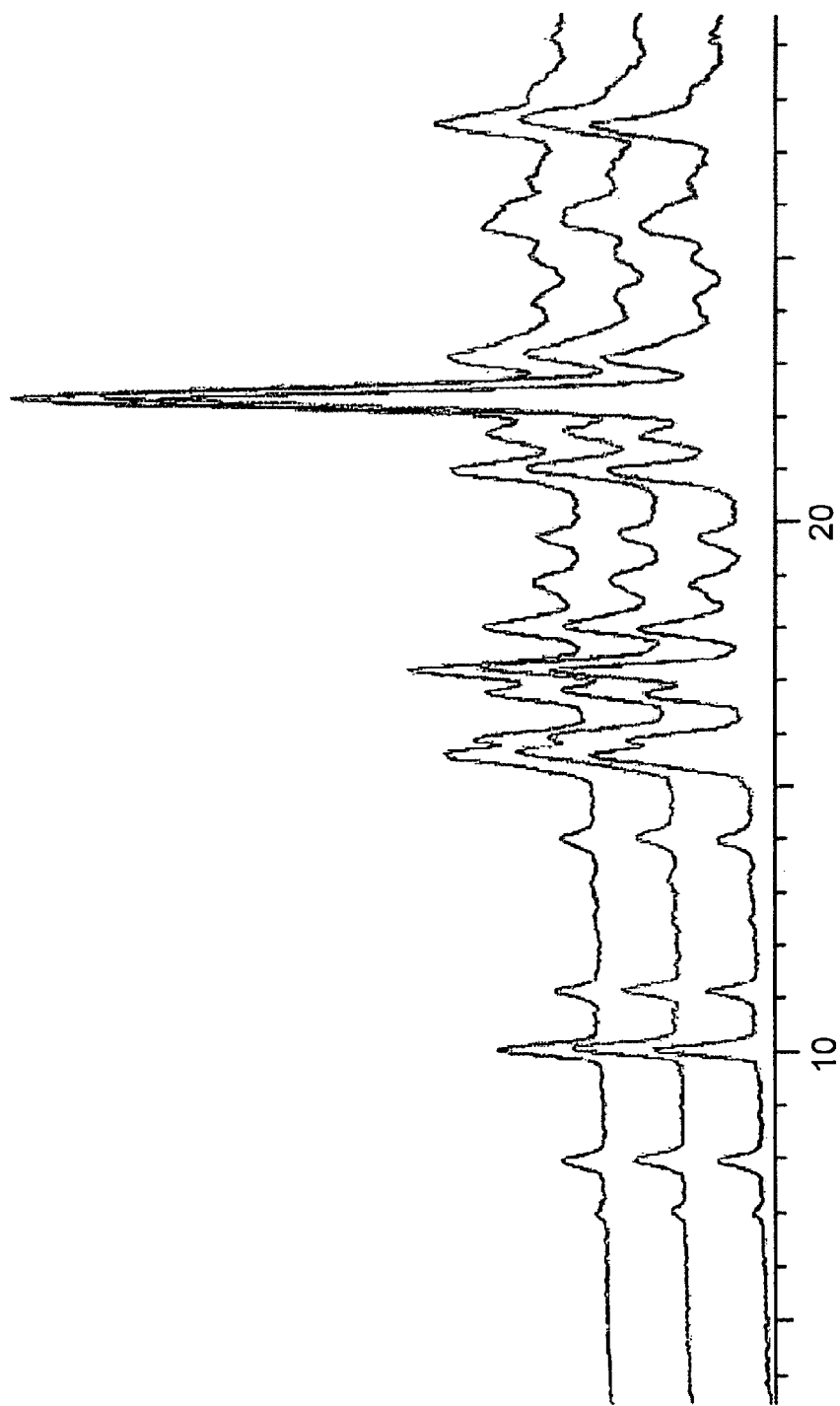
FIG. 10 shows a low resolution X-ray Powder Diffraction diffractograms for Batches 4-6.
Figure 11:
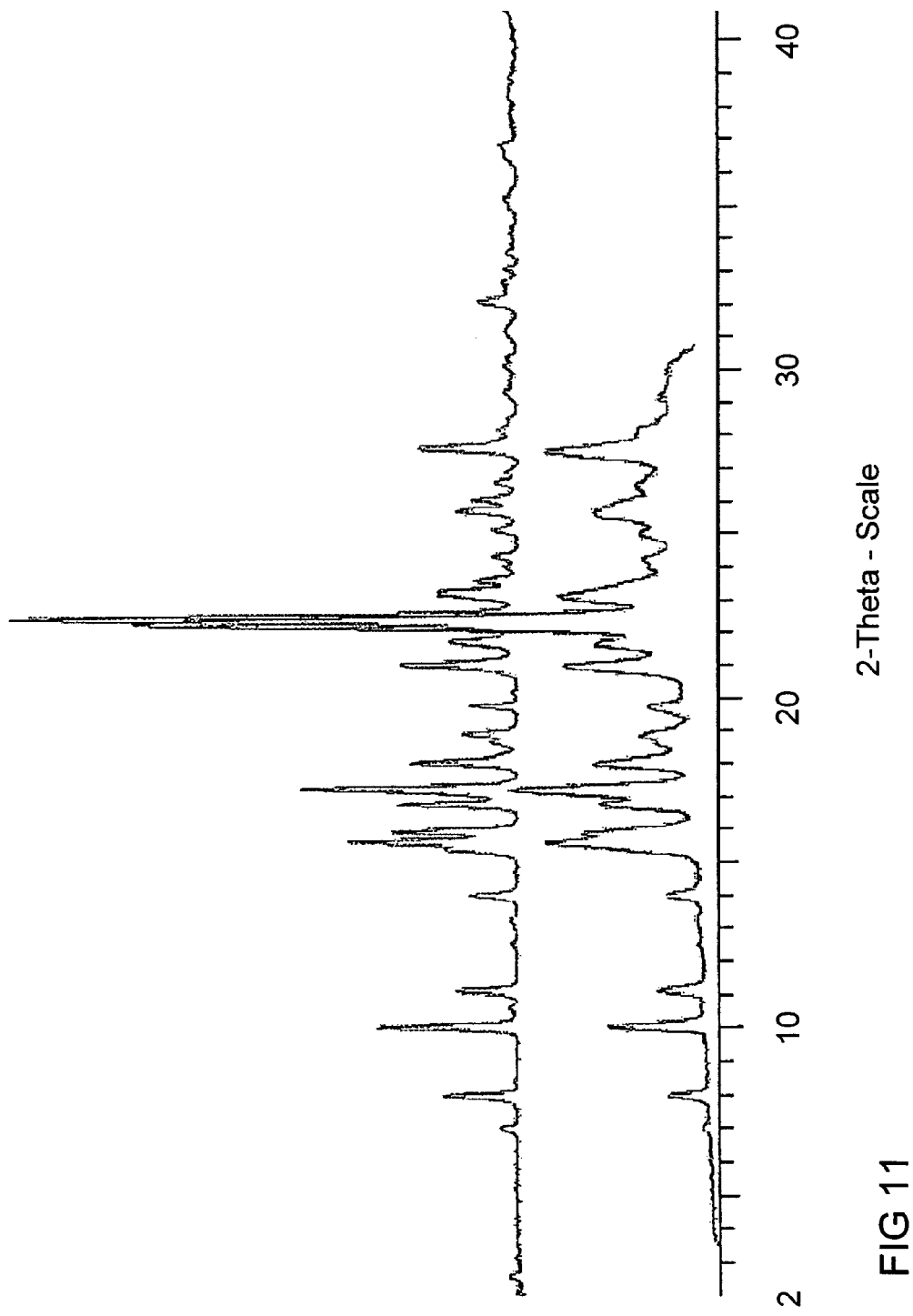
FIG. 11 shows an overlay of the high resolution and low resolution X-ray Powder Diffraction diffractograms for Batch 4.

Low resolution XRPD traces (Condition 2) were also collected using the Bruker GADDS diffractometer, so that reference patterns were available for the polymorphism screen analysis. An overlay of the traces for Batches 4-6 is shown in FIG. 10 and a comparison of the high resolution and low resolution traces for Batch 4 is shown in FIG. 11.

Figure 12:
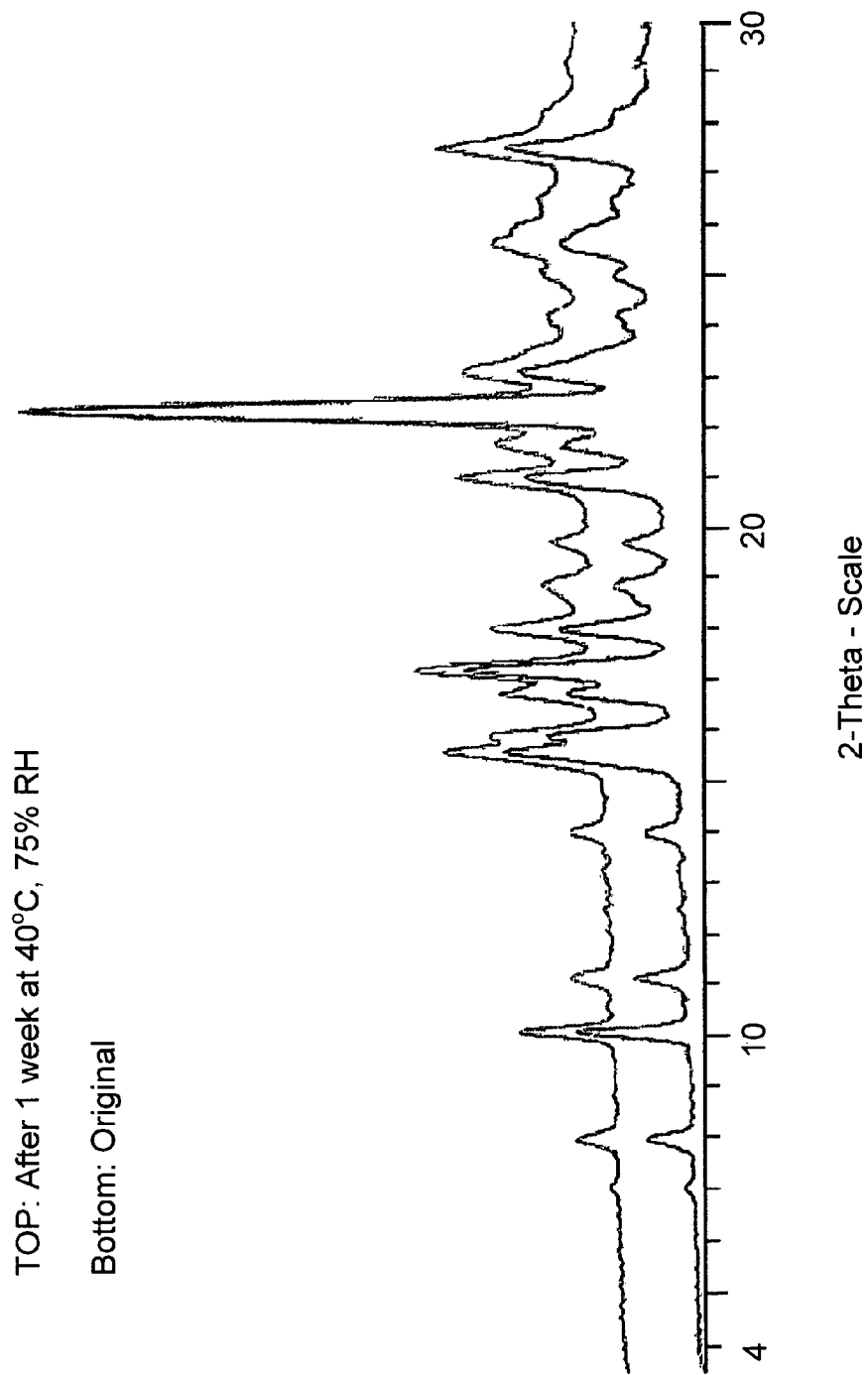
FIG. 12 shows X-ray Powder Diffraction traces for Batch 4 before and after storage at 40° C. and 75% relative humidity for 1 week.
Figure 13:
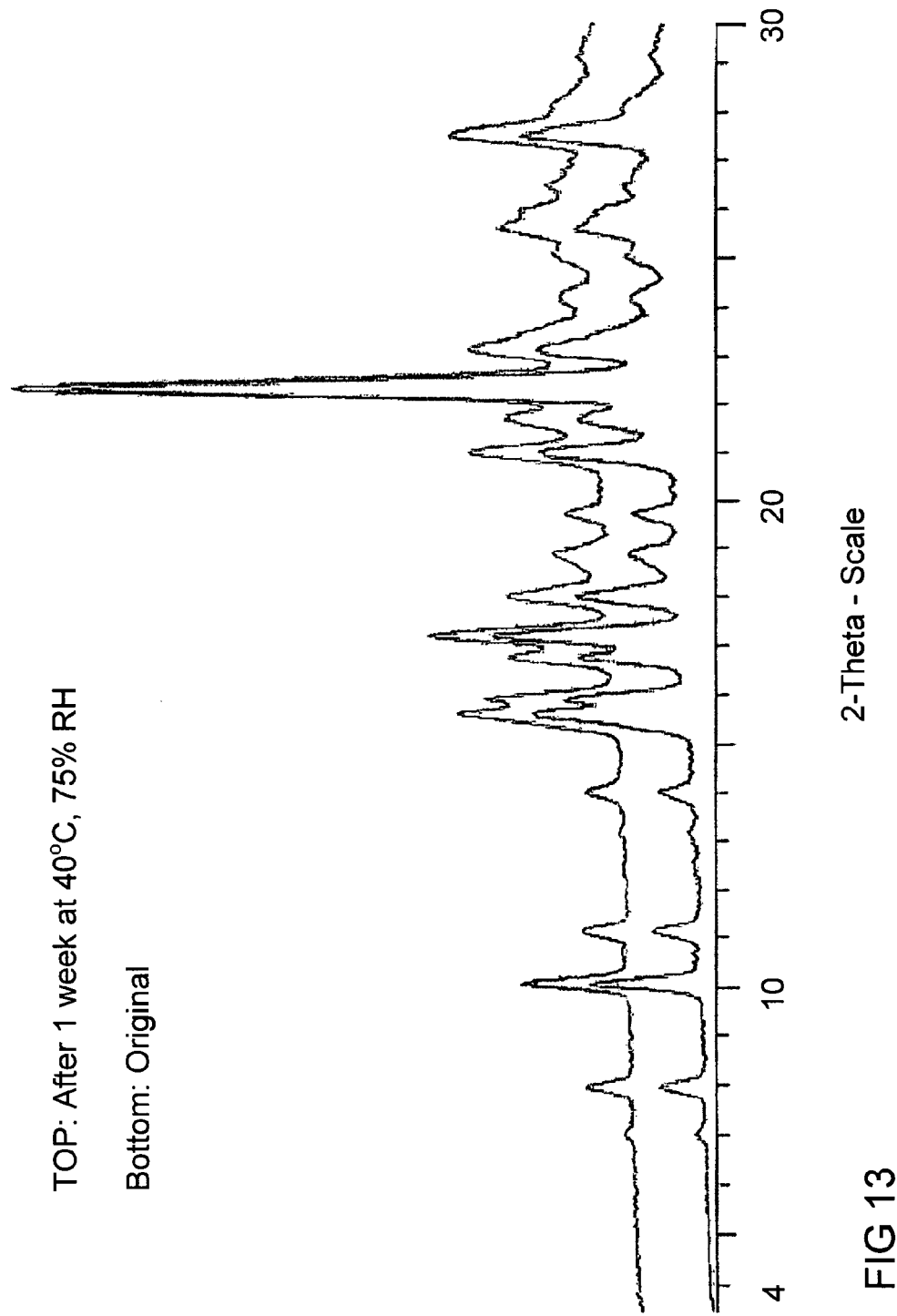
FIG. 13 shows X-ray Powder Diffraction traces for Batch 5 before and after storage at 40° C. and 75% relative humidity for 1 week.
Figure 14:
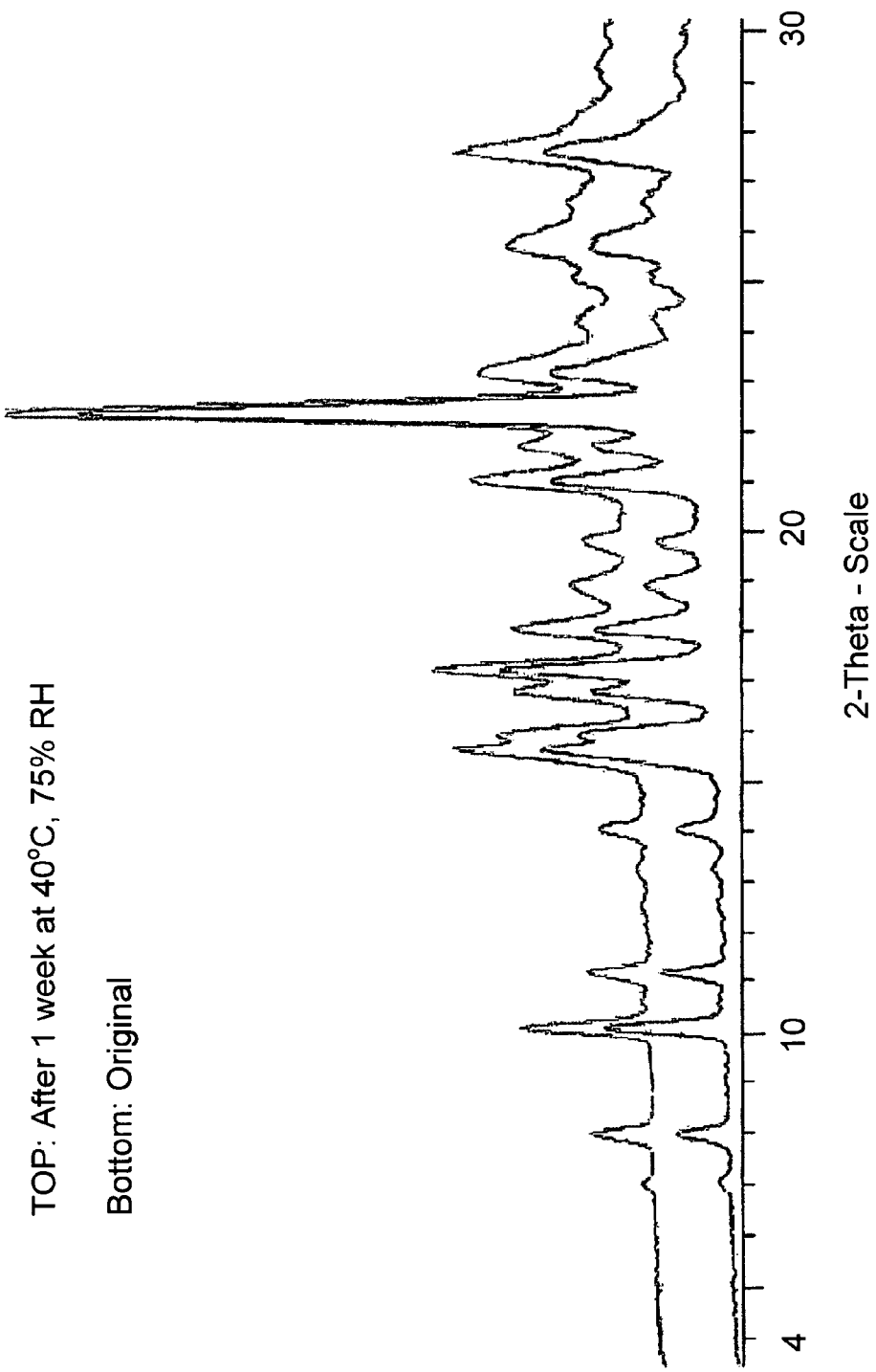
FIG. 14 shows X-ray Powder Diffraction traces for Batch 6 before and after storage at 40° C. and 75% RH for 1 week.

The samples which had been prepared for the collection of low resolution XRPD traces were placed in a chamber maintained at 40° C. and 75% relative humidity. After one week the samples were reanalysed by low resolution XRPD (Condition 2), to check for phase changes. The results, in comparison with the initial XRPD trace are shown in FIG. 12 to FIG. 14. It can be seen that no phase change has occurred, and that citrate salts of the invention are stable for at least one week under these conditions.

Example 8

Nuclear Magnetic Resonance (NMR) Studies $^{1}$H NMR spectra were collected on a Bruker 400 MHz instrument equipped with an autosampler and controlled by a DRX400 console. Automated experiments were acquired using ICON-NMR v4.0.4 (build 1) running with Topspin v 1.3 (patch level 8) using the standard Bruker loaded experiments. Samples were prepared in d6-DMSO or D$_2$O. Off-line analysis was carried out using ACD SpecManager v 9.09 (build 7703).

Figure 22:
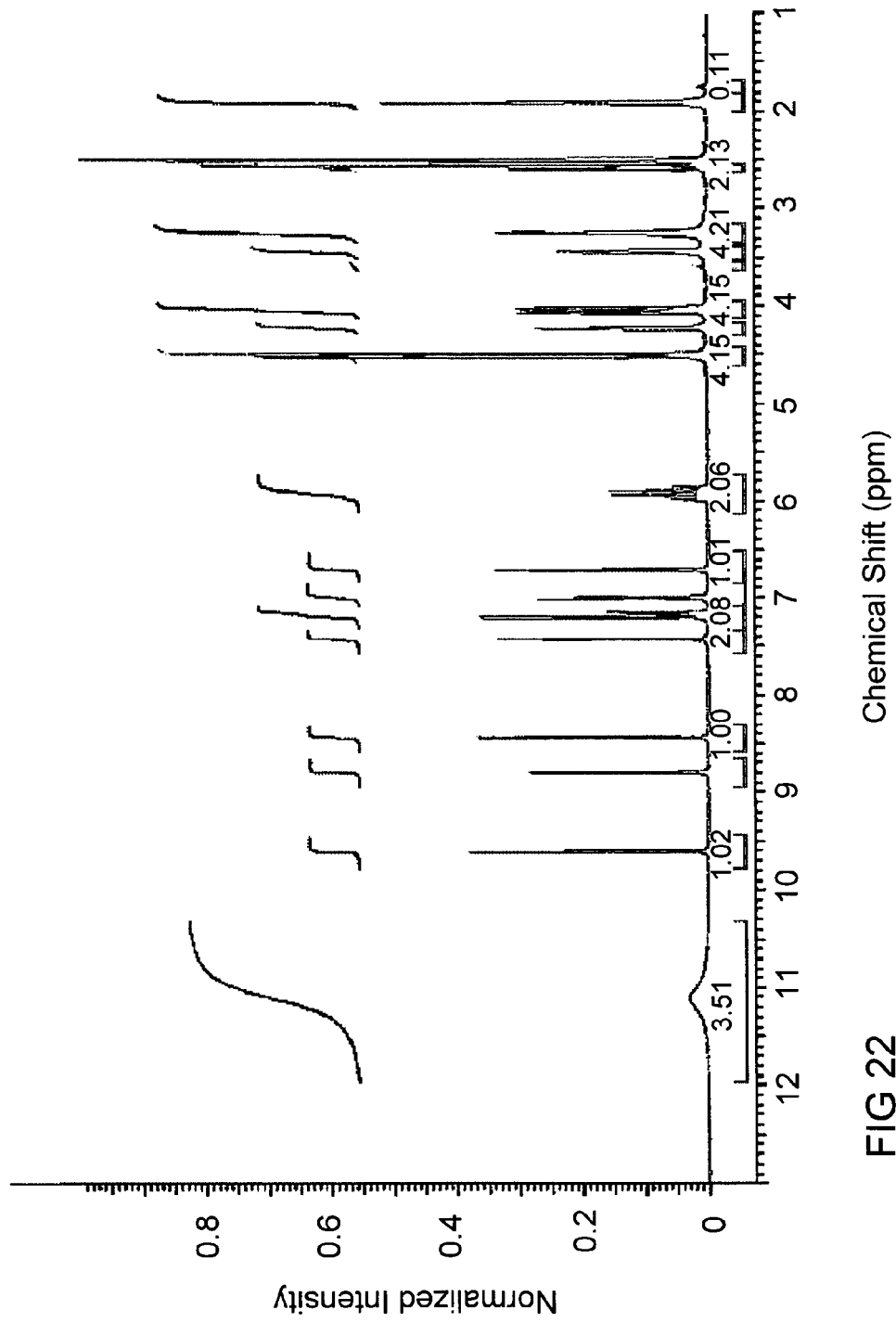
FIG. 22 shows a $^1$H NMR spectrum for Batch 4 in d6-DMSO.
Figure 23:
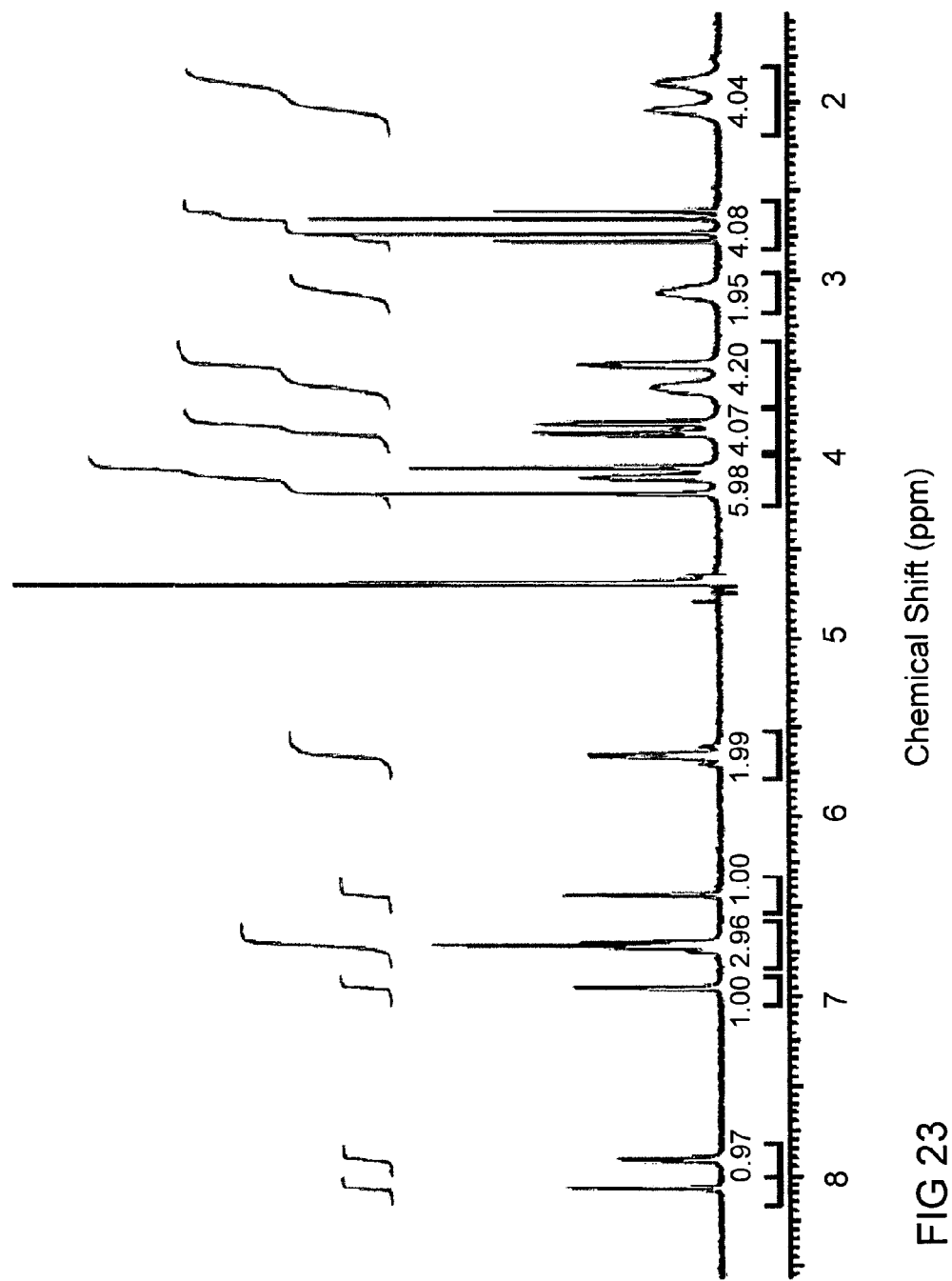
FIG. 23 shows a $^1$H NMR spectrum for Batch 4 in D$_2$O.

$^{1}$H NMR shows that all three samples are of the same compound. The determination of the stoichiometry of the citrate was carried out by integration of the signals of the counter-ion. However, these appear under the DMSO signal in the spectrum (Batch 4, FIG. 22), and as a result the integration of the signals of the citric acid could not be performed. FIG. 23 shows the $^{1}$H-NMR of Batch 4 in D$_2$O. In this solvent, the integration of the signal of the citric acid showed the stoichiometry to be 1:1 as expected.

Example 9

Differential Scanning Calorimetry (DSC) and Thermo-Gravimetric Analysis (TGA)

Differential Scanning Calorimetry (DSC) data were collected on a Mettler DSC 823e equipped with a 34 position auto-sampler. The instrument was calibrated for energy and temperature using certified indium. Typically 0.5-3 mg of each sample, in a pin-holed aluminium pan, was heated at 10° C.min$^{-1}$ from 25° C. to 350° C. A nitrogen purge at 50 ml.min$^{-1}$ was maintained over the sample. The instrument control and data analysis software was STARe v9.10.

Thermogravimetric Analysis (TGA) data were collected on a Mettler TGA/SDTA 851e equipped with a 34 position autosampler. The instrument was temperature calibrated using certified indium. Typically 5-30 mg of each sample was loaded onto a pre-weighed aluminium crucible and was heated at 10° C.min$^{-1}$ from ambient temperature to 350° C. A nitrogen purge at 50 ml.min$^{-1}$ was maintained over the sample. The instrument control and data analysis software was STARe v9.10.

Figure 15:
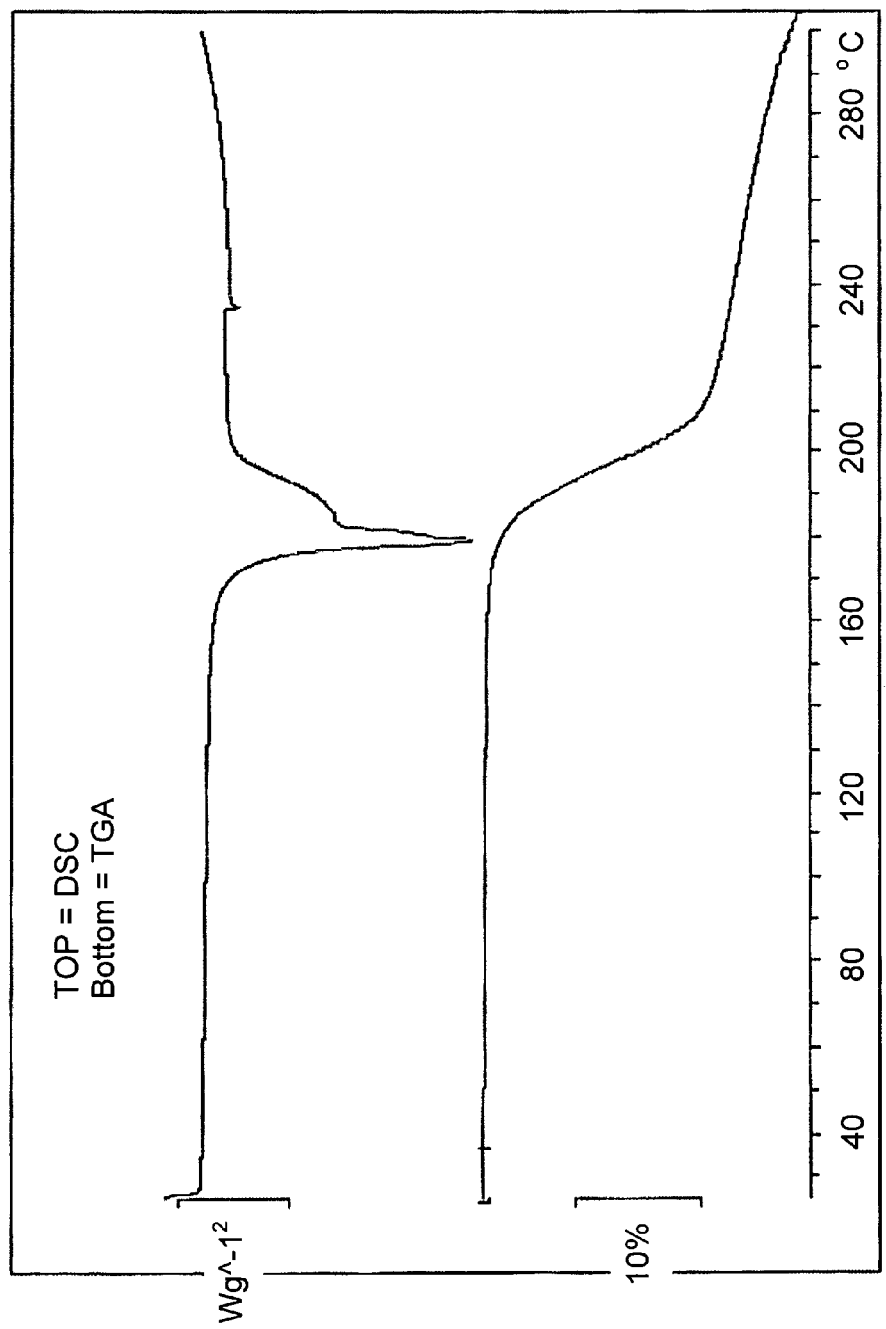
FIG. 15 shows a Differential Scanning calorimetry (DSC, top) and Thermogravimetric Analysis (TGA) data for Batch 4.

The DSC trace for Batch 4 (FIG. 15) shows that there is a significant thermal event at 176° C. There is a corresponding weight loss of ~20% seen in the TGA (FIG. 15). This weight loss, together with the complex shape of the DSC endotherm, indicates that gross degradation is occurring >176° C. Without wishing to be bound by theory, this may be indicative of the dissociation of the salt and the subsequent degradation of the citric acid.

Figure 16:
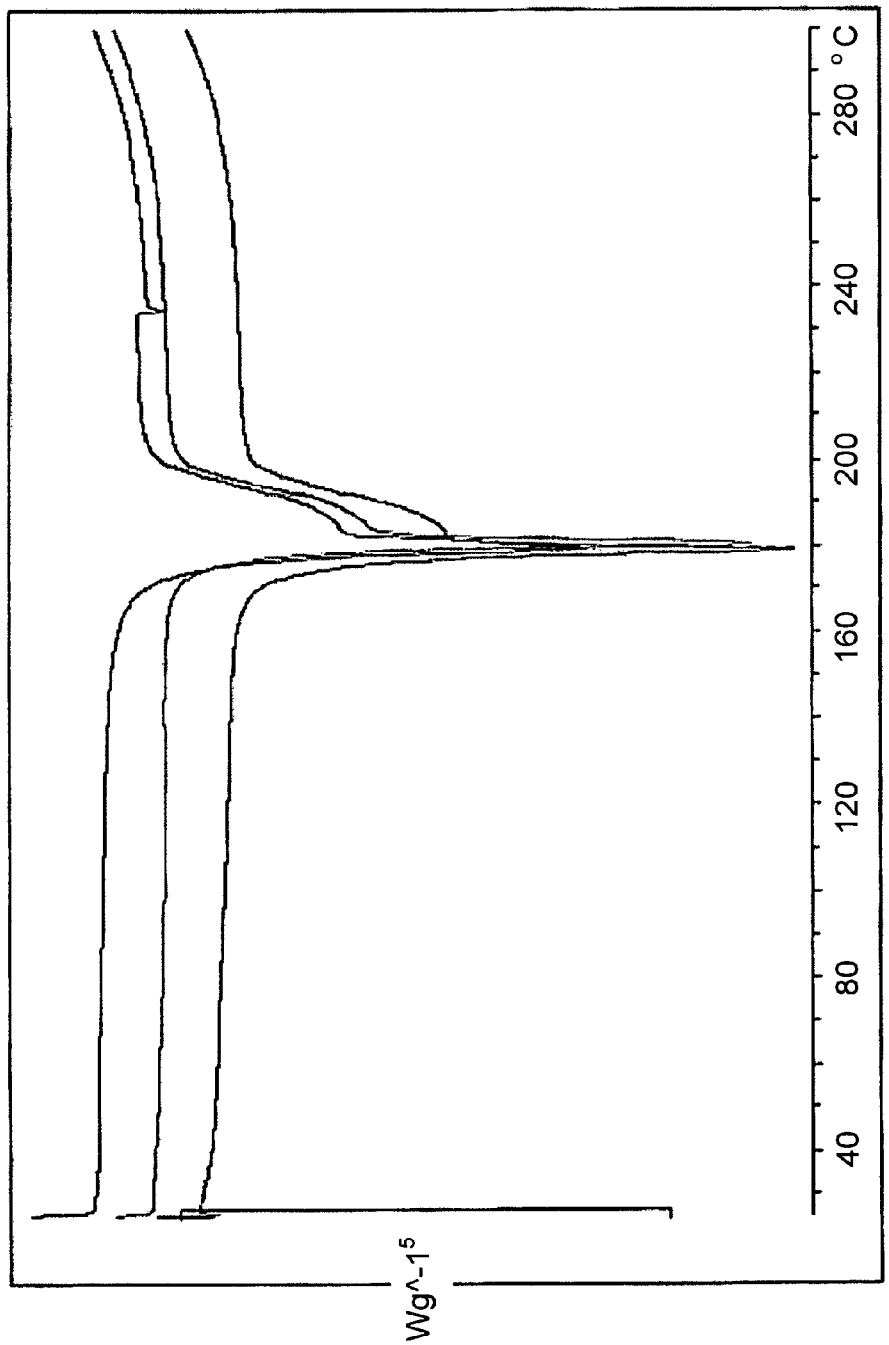
FIG. 16 shows an overlay of DSC traces for Batches 4-6.
Figure 17:
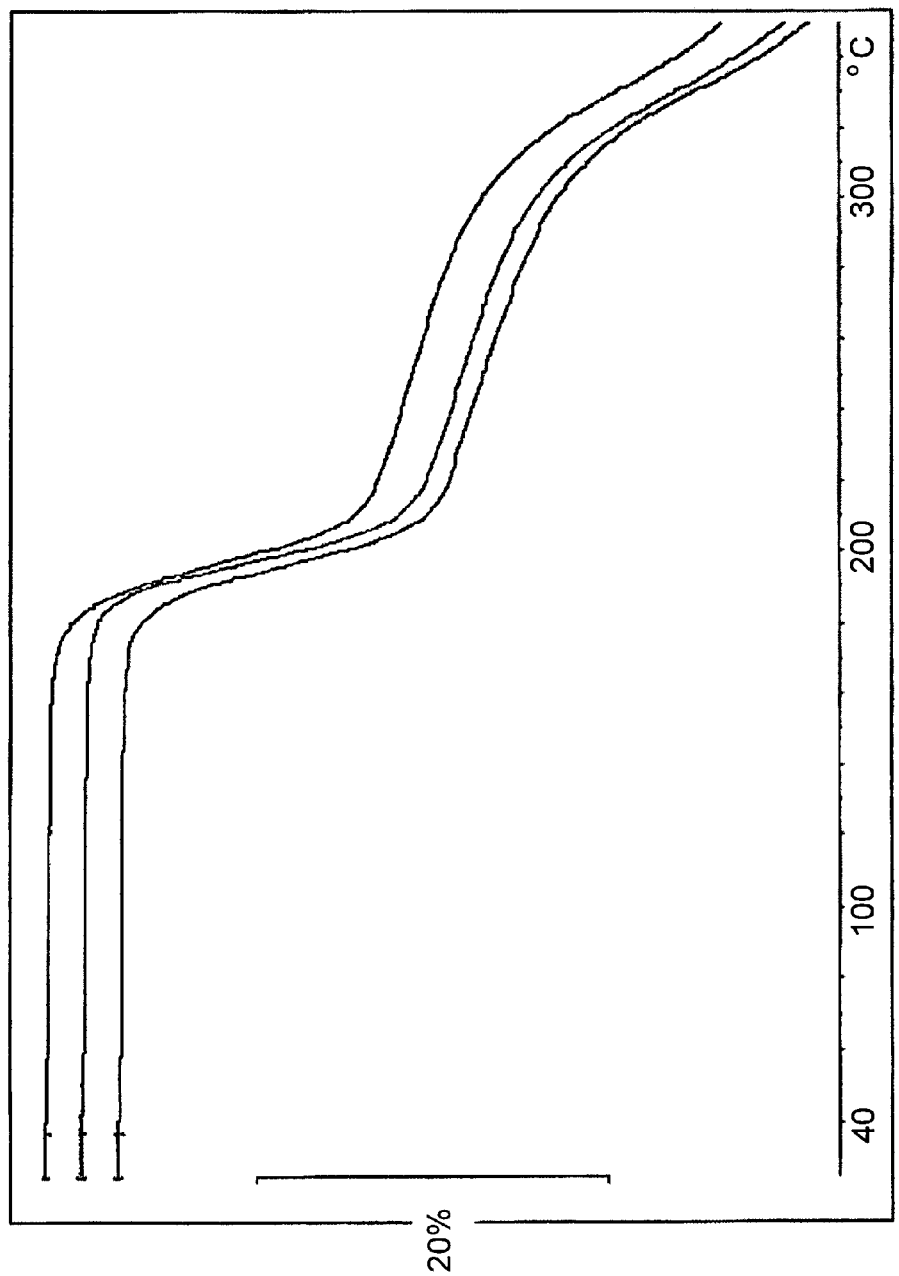
FIG. 17 shows an overlay of TGA traces for Batches 4-6.

Batches 5 and 6 showed similar DSC and TGA traces (FIGS. 16 and 17 show overlays of DSC and TGA data, respectively).

Example 10

Gravimetric Vapour Sorption (GVS)

Sorption isotherms were obtained using a SMS DVS Intrinsic moisture sorption analyser, controlled by SMS Analysis Suite software. The sample temperature was maintained at 25° C. by the instrument controls. The humidity was controlled by mixing streams of dry and wet nitrogen, with a total flow rate of 200 ml.min$^{-1}$. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range.

TABLE 3

Method Parameters for SMS DVS Intrinsic Experiments

| Parameters | Values |
| --- | --- |
| Adsorption—Scan 1 | 40-90 |
| Desorption/Adsorption—Scan 2 | 90 - Dry, Dry - 40 |
| Intervals (% RH) | 10 |
| Number of Scans | 2 |
| Flow Rate (ml · min$^{-1}$) | 200 |
| Temperature (° C.) | 25 |
| Stability (° C. · min$^{-1}$) | 0.2 |
| Sorption Time (hours) | 6 hour time out |

Figure 18:
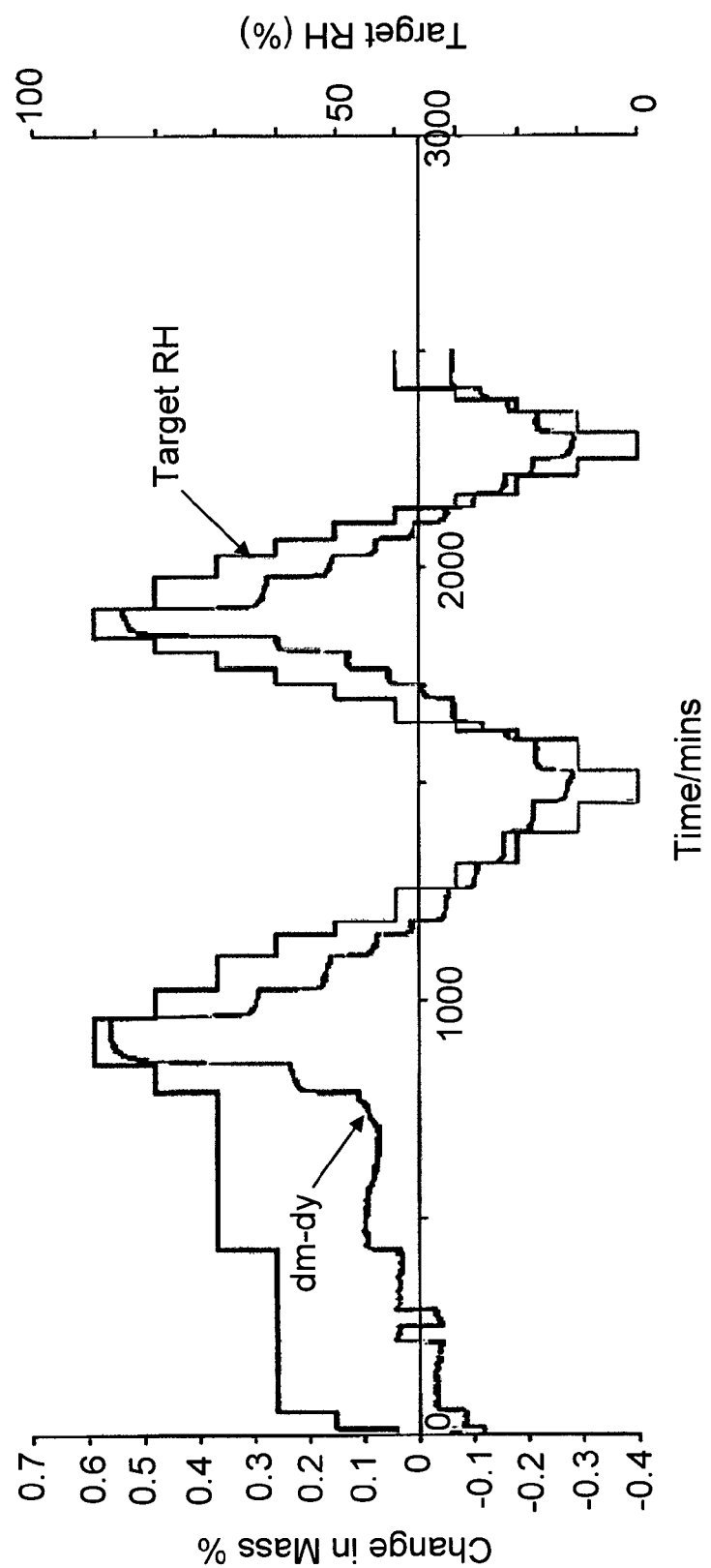
FIG. 18 shows a Gravimetric Vapour Sorption kinetic plot for Batch 4.

The hygroscopicity of the citrate was investigated by carrying out a gravimetric vapour sorption experiment on Batch 4. A sample of approximately 20 mg was held at 25° C. whilst the humidity of its environment was changed through two complete cycles. The kinetic plot shown in FIG. 18 shows that the sample of Batch 4 reaches equilibrium weight at each % RH step. The sample takes longer to reach equilibrium in the early stages of the experiment. This may be due to displacement of residual solvent.

Figure 19:
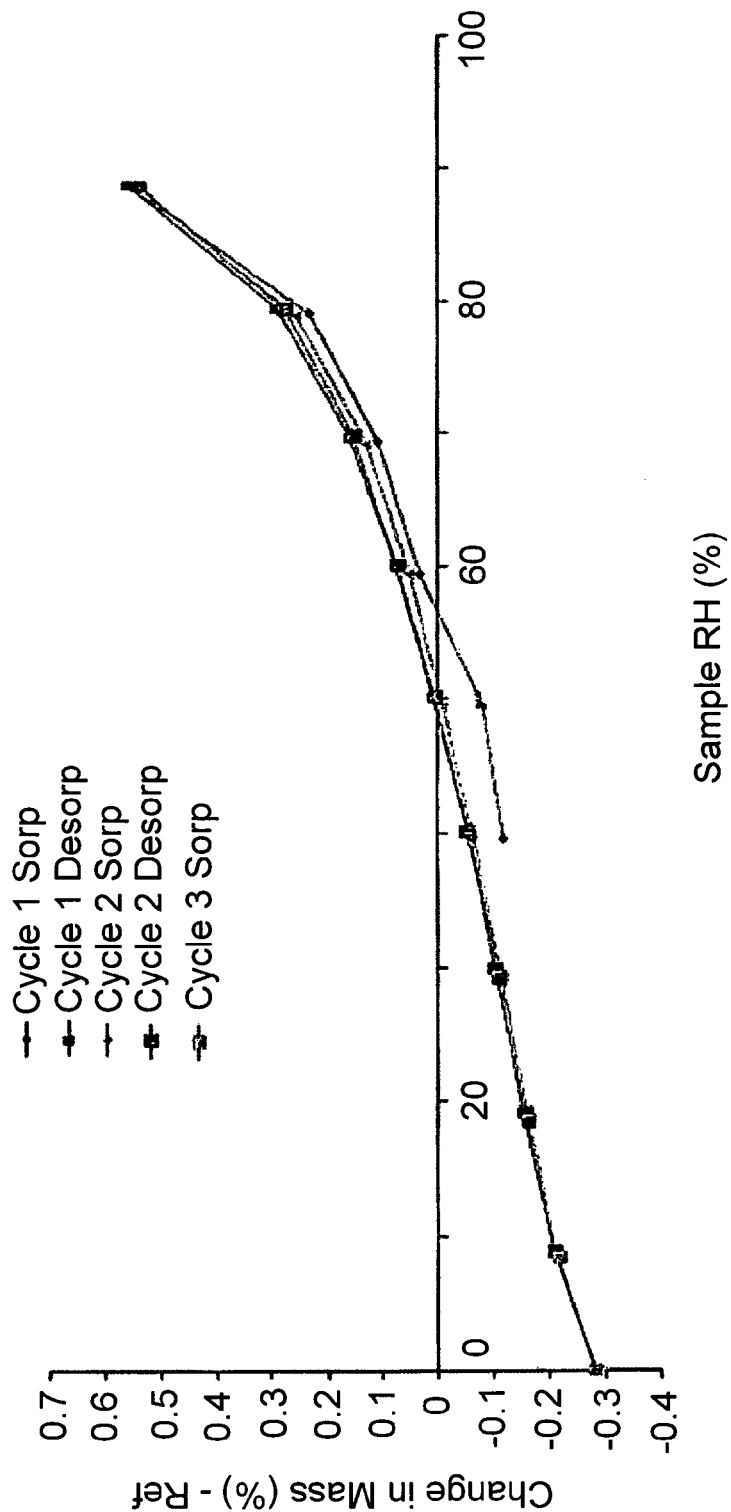
FIG. 19 shows a Gravimetric Vapour Sorption isotherm plot for Batch 4.

The isotherm plot shown in FIG. 19, shows that the sample takes up <0.6% water between 40% RH and 90% RH. The maximum weight difference (between 0% RH and 90% RH) is less than 1% w/w which indicates that the citrate is is not hygroscopic. In addition, there is no evidence for the existence of a hydrated form of the citrate.

TABLE 4

Isotherm Weight Values for the GVS of Batch 4

| | Target RH (%) | Sorp Mass Change (%) | | Target RH (%) | Sorp Mass Change (%) |
|---|---|---|---|---|---|
| Cycle 1 adsorption | 40.0 | −0.1186 | Cycle 2 desorption | 40.0 | −0.0643 |
| | 50.0 | −0.0817 | | 50.0 | −0.0100 |
| | 60.0 | 0.0329 | | 60.0 | 0.0513 |
| | 70.0 | 0.1086 | | 70.0 | 0.1281 |
| | 80.0 | 0.2342 | | 80.0 | 0.2567 |
| | 90.0 | 0.5631 | | 90.0 | 0.5397 |
| Cycle 1 desorption | 90.0 | 0.5631 | Cycle 2 desorption | 90.0 | 0.5397 |
| | 80.0 | 0.2905 | | 80.0 | 0.2771 |
| | 70.0 | 0.1610 | | 70.0 | 0.1535 |
| | 60.0 | 0.0743 | | 60.0 | 0.0738 |
| | 50.0 | 0.0100 | | 50.0 | 0.0045 |
| | 40.0 | −0.0548 | | 40.0 | −0.0528 |
| | 30.0 | −0.1076 | | 30.0 | −0.1032 |
| | 20.0 | −0.1545 | | 20.0 | −0.1565 |
| | 10.0 | −0.2093 | | 10.0 | −0.2093 |
| | 0.0 | −0.2816 | | 0.0 | −0.2836 |
| Cycle 1 readsorption | 0.0 | −0.2816 | Cycle 2 readsorption | 0.0 | −0.2863 |
| | 10.0 | −0.2138 | | 10.0 | −0.2168 |
| | 20.0 | −0.1620 | | 20.0 | −0.1630 |
| | 30.0 | −0.1146 | | 30.0 | −0.1116 |
| | 40.0 | −0.0643 | | 40.0 | −0.0653 |

Figure 20:
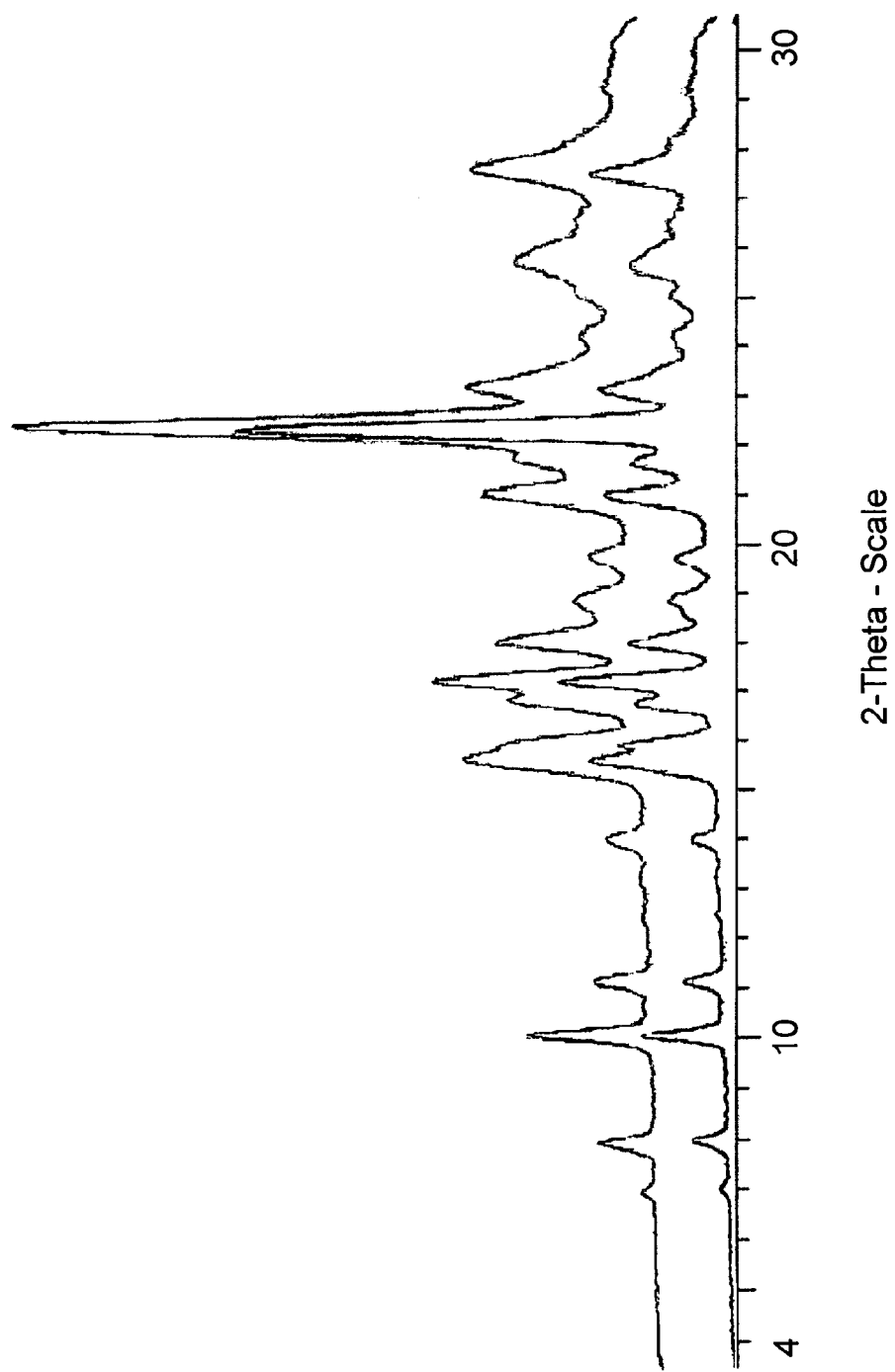
FIG. 20 shows X-ray Powder Diffraction traces for Batch 4 before and after the Gravimetric Vapour Sorption experiment was conducted.

At the end of the GVS experiment, the sample was retrieved and analysed by XRPD to check for any overall phase change. The results (FIG. 20) show that there is no overall phase change.

Example 11

Chemical Purity Determination by High Performance Liquid Chromatography (HPLC)

Purity analysis was performed on an Agilent HP1100 series system equipped with a diode array detector and using ChemStation software vB.02.01-SR1. The parameters used are summarized in Table 5.

TABLE 5

HPLC Method Parameters for Chemical Purity Determinations

| Sample Preparation: | 0.5 mg/ml in acetonitrile:water 1:1 v/v |
| Column: | Phenomenex Luna C18 (2), 150 × 4.6 mm, 5 um |
| Column Temperature (° C.): | 25 |
| Injection (uL): | 5 |
| Detection Wavelength, Bandwidth (nm): | 255, 90 |
| Flow rate (ml · min$^{-1}$): | 1 |
| Phase A: | 0.1% TFA in water |
| Phase B: | 0.085% in acetonitrile |

Timetable:

| Time (min) | % Phase A | % Phase B |
|---|---|---|
| 0 | 95 | 8 |
| 25 | 5 | 95 |
| 25.2 | 95 | 5 |
| 30 | 95 | 5 |

The chemical purity of Batches 4-6 of the citrate was determined using this HPLC procedure. The numerical results are shown in Table 6.

TABLE 6

Purity Determination Results

| Sample | Batch 4 | Batch 5 | Batch 6 |
|---|---|---|---|
| Dissolving solvent | | AcN:H$_2$O 1:1 v/v | |
| Retention Time | 2.76 | 2.76 | 2.76 |
| Parent Peak Area | 1431.73 | 1299.9 | 1368.57 |
| RRT | Area % | Area % | Area % |
| 0.97 | 0.61 | 0.41 | 0.48 |
| 1.00 | 98.12 | 98.45 | 98.37 |
| 1.04 | 0.14 | 0.16 | 0.14 |
| 1.05 | 0.22 | 0.13 | 0.20 |
| 1.07 | 0.18 | 0.13 | 0.14 |
| 1.12 | 0.28 | 0.31 | 0.28 |

As can be seen, the measured purity of each sample is greater than 98.1%.

Example 12

Solubility and Polymorphism Assessment

For each solvent investigated, approximately 8 mg of compound 1 was weighed into an 8 ml screw top glass vial. The solvent was added in 10 volume aliquots and the mixture sonicated and warmed (with a hot-air gun) to encourage dissolution. If dissolution was not achieved after the addition of 100 volumes of solvent, a further 100 volumes was added. The details of each experiment and the observations (Table 7) show that total dissolution was only achieved in water.

TABLE 7

Details of Solubility Assessment

| Sample ID | Input batch | Wt (mg) | Solvent (vols) | 10 | 20 | 30 | 40 | 50 | 60 | 70 | 80 | 90 | 100 | 200 |
|---|---|---|---|---|---|---|---|---|---|---|---|---|---|---|
| HC531-16-01 | 4 | 8.1 | Toluene | x | x | x | x | x | x | x | x | x | x | x |
| HC531-16-02 | 4 | 8.0 | TBME | x | x | x | x | x | x | x | x | x | x | x |
| HC531-16-03 | 4 | 7.3 | Ethyl acetate | x | x | x | x | x | x | x | x | x | x | x |
| HC531-16-04 | 4 | 7.9 | i-propyl acetate | x | x | — | x | — | x | — | x | — | x | x |
| HC531-16-05 | 5 | 7.9 | THF | x | x | x | x | — | x | — | x | — | x | x |
| HC531-16-06 | 5 | 8.2 | IPA | x | x | x | x | — | x | — | x | — | x | x |
| HC531-16-07 | 5 | 8.2 | MEK | x | x | x | x | x | — | x | — | x | x | x |
| HC531-16-08 | 5 | 8.2 | Acetone | x | x | — | x | — | x | — | x | — | x | x |

TABLE 7-continued

Details of Solubility Assessment

| Sample ID | Input batch | Wt (mg) | Solvent (vols) | 10 | 20 | 30 | 40 | 50 | 60 | 70 | 80 | 90 | 100 | 200 |
|---|---|---|---|---|---|---|---|---|---|---|---|---|---|---|
| HC531-16-09 | 5 | 9.7 | Ethanol | x | x | x | x | — | x | — | x | — | x | x |
| HC531-16-10 | 5 | 9.6 | Acetonitrile | x | x | x | x | — | x | — | x | — | x | x |
| HC531-16-11 | 5 | 7.8 | Water | H | — | — | — | — | — | — | — | — | — | — |

Figure 21:
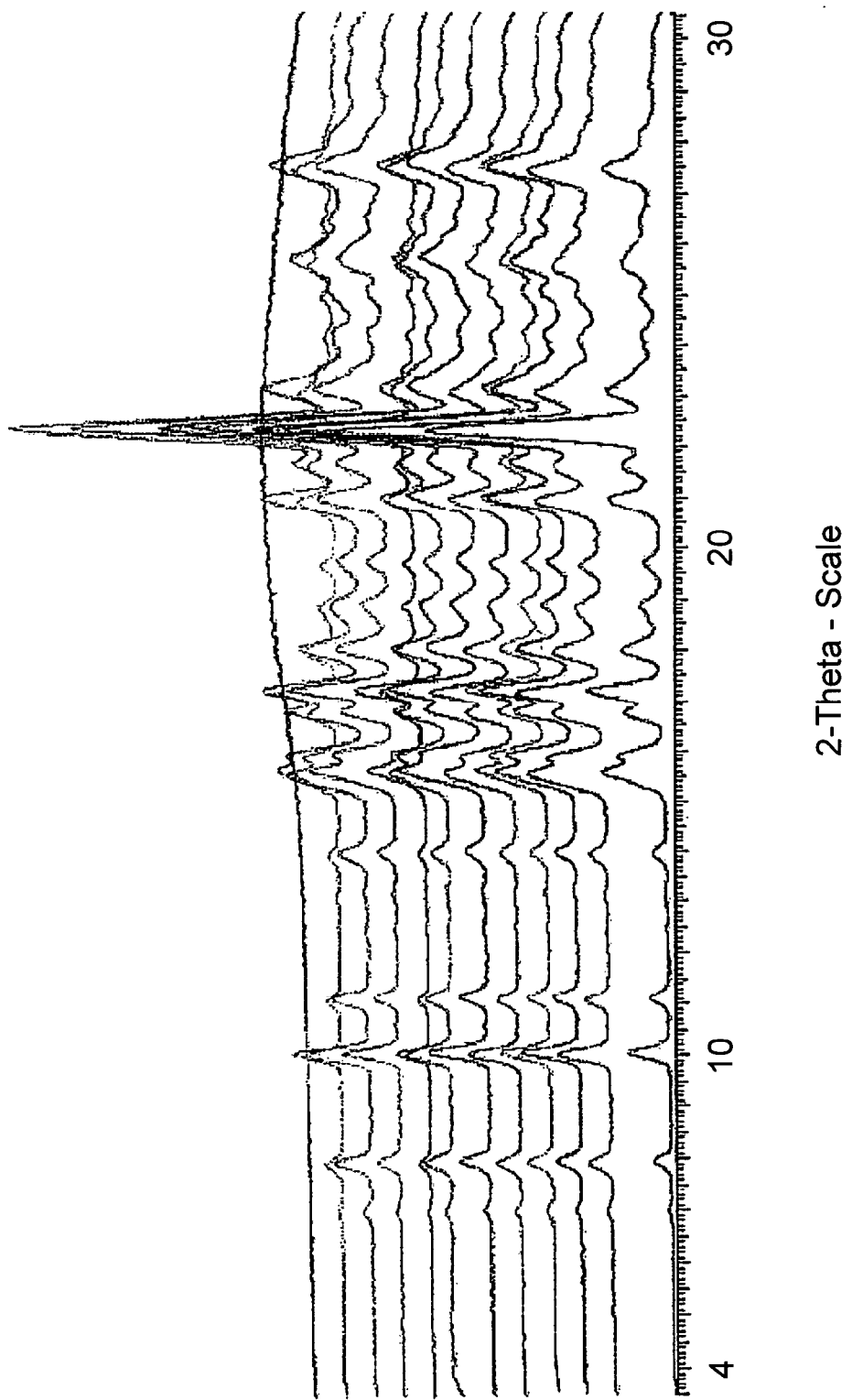
FIG. 21 shows X-ray Powder Diffraction traces of samples from the solubility screen.

The vials were then placed in a humidity chamber and subjected to cycles of 25° C./50° C. (8 hour cycles) for 24 hours. At the end of this time the samples were examined and then left with loosened lids to allow for evaporation of the solvent. Those samples which had dried out were then transferred to a quartz array, whilst those for which there was still solvent present, were filtered under vacuum onto a sinter. The samples were then analysed by XRPD to assess their crystalline state and form. The results of the XRPD analysis (FIG. 21) show that (with water as the single exception) all the samples were of Form 1. The sample obtained from aqueous solution was amorphous (FIG. 21, top trace shows no sharp peaks).

The solubility of compound 1 citrate in organic solvents has proved to be extremely limited. The lack of colouration in the solvents in contact with the yellow crystals indicates that solubility was minimal. All the crystalline residues from the organic solvent screening samples were Form 1. The citrate was found to dissolve in water at the 100 mg.ml$^{-1}$ level. The solid recovered by allowing the solution to evaporate was found to be amorphous. The solubility screen did not reveal the existence of any solvates or polymorphs of the citrate salts.

The results of the Examples 1-12 are summarized in the table below.

TABLE 8

Summary of batch Characterization

| | Batch 4 | Batch 5 | Batch 6 |
|---|---|---|---|
| XRPD | Crystalline Form 1 | Crysatlline Form 1 | Crystalline Form 1 |
| Phase Stability 1 wk @ 40° C./75% RH | Crystalline Form 1 | Crystalline Form 1 | Crystalline Form 1 |
| Gravimetric Vapour Sorption | Max weight change <1% No phase changes | — | — |
| Thermogravimetric Analysis | −0.4% w/w ambient to 160° C. −20% w/w 160 to 250° C. | −0.4% w/w ambient to 160° C. −21% w/w 160 to 250° C. | −0.3% w/w ambient to 160° C. −20% w/w 160 to 250° C. |
| Differential Scanning Calorimetry | Complex endotherm onset 176° C. | Complex endotherm onset 178° C. | Complex endotherm onset 176° C. |
| Purity by HPLC | 98.12% a/a | 98.45% a/a | 98.37% a/a |

The details of specific embodiments described in this invention are not to be construed as limitations. Various equivalents and modifications may be made without departing from the essence and scope of this invention, and it is understood that such equivalent embodiments are part of this invention.

What is claimed is:

1. A crystalline citrate salt of 9E-15-(2-pyrrolidin-1-yl-ethoxy)-7,12,25-trioxa-19,21,24-triaza-tetracyclo[18.3.1.1(2,5).1(14,18)]hexacosa-1(24),2,4,9,14,16,18(26),20,22-nonaene which shows on X-ray diffraction at least one peak on the 2theta scale selected from the group consisting of 10.0°±0.5°, 15.6°±0.5°, 17.2°±0.5° and 22.4°±0.5°.

2. The salt according to claim 1 wherein the salt is the 1:1 salt.

3. The salt according to claim 1 which shows on X-ray diffraction a peak on the 2theta scale at 22.4°±0.5°.

4. The salt according to claim 3 which also shows on X-ray diffraction peaks on the 2theta scale at 10.0°±0.5°, 15.6°±0.5° and 17.2°±0.5°.

5. The salt according to claim 1 which shows on X-ray diffraction at least four peaks on the 2theta scale selected from the group consisting of 7.9°±0.5°, 10.0°±0.5°, 15.6°±0.5°, 15.9°±0.5°, 16.8°±0.5°, 17.2°±0.5°, 21.1°±0.5°, and 22.4°±0.5°.

6. The salt according to claim 1 which shows on X-ray diffraction at least 6 peaks on the 2theta scale selected from the group consisting of 7.9°±0.5°, 10.0°±0.5°, 15.6°±0.5°, 15.9°±0.5°, 16.8°±0.5°, 17.2°±0.5°, 21.1°±0.5°, and 22.4°±0.5°.

7. The salt according to claim 1 which shows on X-ray diffraction peaks on the 2theta scale at 7.9°±0.5°, 10.0°±0.5°, 15.6°±0.5°, 15.9°±0.5°, 16.8°±0.5°, 17.2°±0.5°, 21.1°±0.5°, and 22.4°±0.5°.

8. The salt according to claim 7 which also shows on X-ray diffraction peaks on the 2theta scale at 11.1°±0.5°, 18.1°±0.5°, 21.8°±0.5°, 23.2°±0.5°, and 27.6°±0.5°.

9. The salt according to claim 8 which also shows on X-ray diffraction peaks on the 2theta scale at 7.0°±0.5°, 14.0°±0.5°, 19.0°±0.5°, 19.8°±0.5°, 23.6°±0.5°, 24.3°±0.5°, 25.2°±0.5°, 25.7°±0.5°, 26.1°±0.5°, 26.5°±0.5°, and 32.1°±0.5°.

10. A pharmaceutical composition comprising a salt according to claim 1.

11. A method of treating a proliferative disorder selected from the group consisting of rheumatoid arthritis, acute myeloid leukemia and erythroleukemia comprising administration of a therapeutically effective amount of a salt according to claim 1 to a patient in need thereof.

12. The method according to claim 11 wherein the proliferative disorder is rheumatoid arthritis.

13. The method according to claim 11 wherein the proliferative disorder is acute myeloid leukemia.

14. The method according to claim 11 wherein the proliferative disorder is erythroleukemia.

* * * * *